(12) United States Patent
Bresnick

(10) Patent No.: US 11,969,330 B2
(45) Date of Patent: Apr. 30, 2024

(54) DEVICE FOR ORIENTING IMPLANTS ONTO IMPLANT INSERTION DEVICES AND FIXING INSERTION DEVICES DURING LOADING

(71) Applicant: Stephen David Bresnick, Encino, CA (US)

(72) Inventor: Stephen David Bresnick, Encino, CA (US)

( * ) Notice: Subject to any disclaimer, the term of this patent is extended or adjusted under 35 U.S.C. 154(b) by 0 days.

(21) Appl. No.: 18/347,511

(22) Filed: Jul. 5, 2023

(65) Prior Publication Data

US 2024/0008969 A1 Jan. 11, 2024

Related U.S. Application Data

(60) Provisional application No. 63/367,695, filed on Jul. 5, 2022.

(51) Int. Cl.
*A61F 2/00* (2006.01)
*A61F 2/12* (2006.01)

(52) U.S. Cl.
CPC .............. *A61F 2/0095* (2013.01); *A61F 2/12* (2013.01)

(58) Field of Classification Search
CPC .................................. A61F 2/0095; A61F 2/12
See application file for complete search history.

(56) References Cited

U.S. PATENT DOCUMENTS

| | | | |
|---|---|---|---|
| 1,351,917 A | 9/1920 | Kuhn | |
| 6,146,418 A | 11/2000 | Berman | |
| 8,206,443 B2 | 6/2012 | Preissman | |
| 8,211,173 B2 | 7/2012 | Keller et al. | |
| 8,315,700 B2 | 11/2012 | Citron et al. | |
| 8,409,279 B2 | 4/2013 | Freund | |
| 8,550,090 B2 | 10/2013 | Keller et al. | |
| 8,555,893 B2 | 10/2013 | Keller et al. | |
| 9,168,126 B2 | 10/2015 | Preissman | |
| 9,402,713 B2 | 8/2016 | Keller et al. | |

(Continued)

FOREIGN PATENT DOCUMENTS

| | | |
|---|---|---|
| WO | 2012177587 A1 | 12/2012 |
| WO | 2016085930 A1 | 6/2016 |
| WO | 2018199929 A1 | 11/2018 |

*Primary Examiner* — Matthew J Lawson
*Assistant Examiner* — Rebecca Lynee Zimmerman
(74) *Attorney, Agent, or Firm* — Womble Bond Dickinson (US) LLP

(57) ABSTRACT

Apparatuses, methods, systems, and kits for facilitating the loading of a prosthesis implant into an implant delivery device for delivering prosthesis implants into surgically-created implant pockets in a subject and for preventing capsular contracture resulting from surgical insertion of prosthesis implants. The loading apparatus may include a receiving portion and, optionally, at least one inclined guide portion. The receiving portion is operable to receive at least a portion of the implant delivery device while the optional at least one inclined guide portion is operable to receive the implant and guide it toward the recessed receiving portion such that the implant is correctly oriented in the implant delivery device. The at least one inclined guide portion may be deployed by operation of a pop-up portion operable to deploy from a substantially flat configuration to an extended deployed configuration comprising at least one inclined guide portion.

19 Claims, 17 Drawing Sheets

(56) References Cited

U.S. PATENT DOCUMENTS

| | | | |
|---|---|---|---|
| 9,414,941 B2 | 8/2016 | Placik et al. | |
| 9,737,395 B2 | 8/2017 | Nguyen et al. | |
| 9,808,284 B2 | 11/2017 | Anderson | |
| 9,808,285 B2 | 11/2017 | Anderson | |
| 10,004,534 B2 | 6/2018 | Anderson | |
| 10,022,475 B2 | 7/2018 | Nguyen et al. | |
| 10,058,415 B2 | 8/2018 | Preissman | |
| 10,092,385 B2 | 10/2018 | Anderson | |
| 10,105,213 B2 | 10/2018 | Weinzweig | |
| 10,136,988 B2 | 11/2018 | Keller et al. | |
| 10,213,294 B2 | 2/2019 | Keller et al. | |
| 11,083,557 B1 * | 8/2021 | Jalota | A61L 27/58 |
| 11,116,620 B1 | 9/2021 | Bresnick | |
| 2007/0276484 A1 | 11/2007 | Abell et al. | |
| 2010/0154803 A1 | 6/2010 | Haworth | |
| 2015/0297339 A1 | 10/2015 | Placik et al. | |

\* cited by examiner

DEVICE FOR ORIENTING IMPLANTS ONTO IMPLANT INSERTION DEVICES AND FIXING INSERTION DEVICES DURING LOADING

CROSS-REFERENCE TO RELATED APPLICATIONS

This application claims the benefit of U.S. Provisional Application Ser. No. 63/367,695, entitled "Device for Orienting Implants Onto Implant Insertion Devices and Fixing Insertion Devices During Loading," filed Jul. 5, 2022, the contents of which is incorporated by reference herein, for all purposes, in its entirety.

FIELD OF TECHNOLOGY

The present disclosure is directed to apparatuses, methods, systems, and kits for the insertion of prosthesis implants into a surgically-created implant pocket of a subject. In some specific instances, the present disclosure is directed to apparatuses, methods, systems, and kits for the insertion of breast implants, including un-filled implants and pre-filled implants such as silicone breast implants and pre-filled saline implants. The present disclosure is further directed to apparatuses, methods, systems, and kits for inserting prosthesis implants in the surgically-created implant pocket of a subject as well as for preventing capsular contracture resulting from surgical insertion of prosthesis implants.

BACKGROUND

During the surgical insertion of prosthesis implants into the surgically-created implant pocket of a subject, it is important to maintain the sterility of the implant. In particular, the sterile implant should be shielded from contamination from surgical handling and the surgical environment including the skin of the subject and potentially the dissection tunnel connecting the incision to the implant pocket. Implant insertion devices may be used to minimize handling of prosthesis implants and to facilitate insertion of the implant into the implant pocket. In such instances, the implant delivery device is loaded with the implant and the surgeon applies mechanical force to the implant delivery device causing the implant to be squeezed or propelled into the implant pocket in the subject. Accordingly, improved methods and devices for loading the implant into the delivery device, for fixing or anchoring the delivery device during loading, and for orienting the implant correctly as it is inserted or loaded into the delivery device are desirable.

Capsular contracture remains the most common complication of aesthetic breast augmentation despite advances in the understanding of the biological processes which appear to be involved. Capsular contracture is characterized by the tightening and hardening of the capsule surrounding the implant. The role of biofilms in capsular contracture has been reported extensively and is believed to play an important role in the pathogenesis of capsular contracture. Recent advances in antibiotic irrigation as well as the use of skin barriers and nipple shields has assisted in the reduction of capsular contracture. Yet, despite these advances, a significant number of women develop capsular contracture following breast augmentation and require revisional surgery or live with discomfort, deformity, or suboptimal results.

Form-stable implant studies with textured devices have shown lower capsular contracture rates compared to smooth round devices. However, anaplastic large cell lymphoma (ALCL) is an indolent lymphoma found in women with textured implants. Biofilm infection is hypothesized to be involved in the development of both capsular contracture and ALCL. It is suspected that a source of the biofilm infection may be microbes from the skin and/or exposed breast tissue of the patient that come in contact with the sterile implant during insertion into the surgically-created implant pocket. In particular, the subject's endogenous flora present at the time of the surgery, including those bacteria that may be present in the dissection tunnel connecting the skin incision to the surgically-created implant pocket or the skin surface itself, may attach to the surface of the implant during placement in the implant pocket. Following insertion of the implant, the bacteria may colonize the surface of the implant and form a biofilm. If the surface of the implant is colonized by a large number of bacteria, the subject's defenses may be overwhelmed and the biofilm may trigger a chronic inflammatory response leading to subsequent fibrosis and accelerated capsular contracture. Accordingly, methods and devices capable of delivering the implant to the implant pocket in the subject while shielding the implant from microbial contamination, including contamination by the endogenous flora of the subject, during delivery and insertion of the implant into the surgically-created implant pocket are desirable. Further, devices and methods for improved or advantageous loading of the delivery devices with the implant are desirable.

BRIEF DESCRIPTION OF THE DRAWINGS

In order to describe the manner in which the advantages and features of the disclosure can be obtained, reference is made to embodiments thereof which are illustrated in the appended drawings. One of skill in the art will understand that the reference numbers in the following figures are repeated throughout FIGS. 1-27 so as to refer to the same or substantially the same features. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
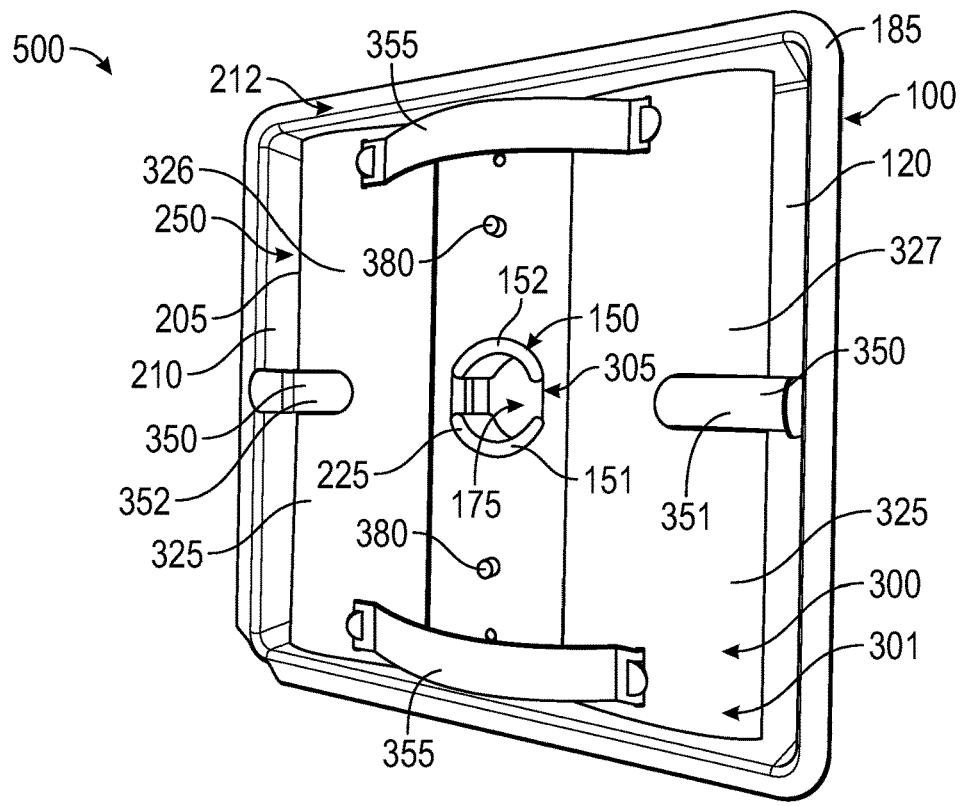
FIG. 1 is a top perspective view of a loading apparatus having a tray portion and a pop-up portion with the pop-up portion in a substantially flat undeployed first configuration, according to an exemplary embodiment of the present disclosure.

It will be appreciated that numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein.

The present disclosure provides apparatuses, methods, systems, and kits for the insertion of prosthesis implants into a surgically-created implant pocket of a subject. In some specific instances, the present disclosure is directed to apparatuses, methods, systems, and kits for the insertion of breast implants, including un-filled implants and pre-filled implants such as silicone breast implants and pre-filled saline implants. The present disclosure is further directed to apparatuses, methods, systems, and kits for inserting prosthesis implants in the surgically-created implant pocket of a subject as well as for preventing capsular contracture resulting from surgical insertion of prosthesis implants. The prosthesis implant may include, for example, filled implants or pre-filled implants, unfilled implants, saline implants, silicone gel implants, textured implants, smooth implants, highly cohesive silicone gel implants, or oil-filled implants. The prosthesis implant may also be, for example, an implantable device, such as a pacemaker or a joint replacement prosthesis, or the prosthesis implant may be a tissue graft, such as an allograft or an autograft. The prosthesis implant may also be a gluteal or buttock implant or a tissue expander.

In some specific instances, the present disclosure is directed to the insertion of breast implants into the implant pocket in a breast of a subject. In such cases, the breast implant may be an un-filled breast implant or may be a pre-filled breast implant such as a pre-filled saline implant or a pre-filled silicone implant. In particular, the presently disclosed apparatuses, methods, systems and kits are well-suited to the delivery of pre-filled breast implants which require an insertion device capable of withstanding and managing the compressive and frictional forces associated with insertion of the pre-filled implant while still being gentle enough so as to not damage the pre-filled implant during delivery to the implant pocket in the subject. The breast implant may also be, for example, a textured breast implant, a smooth breast implant, a highly cohesive silicone gel breast implant, an oil-filled breast implant, or an un-filled saline breast implant. The present disclosure is further directed to apparatuses, methods, systems, and kits for preventing capsular contracture resulting from surgical insertion of breast implants.

According to at least one aspect, the present disclosure provides a loading apparatus for facilitating the loading of an implant into an implant delivery device. Implant delivery devices may be used to minimize handling of prosthesis implants and to facilitate insertion of the implant into the implant pocket. In such instances, the implant delivery device is loaded with the implant and the surgeon applies mechanical force to the implant delivery device causing the implant to be squeezed or propelled into the implant pocket in the subject. In at least some instances the implant delivery device or a portion thereof may be wrapped around an implant in order to load the implant delivery device with the implant. In other instances, the implant may need to be inserted into a pre-formed pocket in the implant delivery device. A general problem with implant delivery devices is that the surgeon often needs to handle the sterile implant in order to load the implant into the implant delivery device and/or to properly orient the implant in the implant delivery device before the implant delivery device can be used to insert the implant into the implant pocket in the subject. The present disclosure, provides loading apparatuses, methods, systems, and kits for loading implant delivery devices that reduce the need for handling the implant, facilitates proper alignment and orientation of the implant within the implant delivery device, and fixes or anchors the implant delivery device during loading of the implant into the implant delivery device.

According to at least one aspect of the present disclosure, a loading apparatus for facilitating the loading of an implant into an implant delivery device is provided. The loading apparatus may include a receiving portion operable to receive at least a portion of the implant delivery device such that movement of the implant delivery device is mitigated during loading of an implant into the delivery device or onto a surface of the delivery device. The loading apparatus may also include a tray portion having an upper surface, a lower surface, and an outer edge extending around the upper and lower surfaces. The tray portion may also include a wall extending around the outer edge such that the wall together with the upper surface forms a reservoir. The loading apparatus may also include a pop-up portion coupled to the tray portion and configured to be retained within the reservoir of the tray portion. The pop-up portion may be operable to deploy from a substantially flat undeployed first configuration to an extended deployed second configuration. The extended second configuration may include at least one inclined guide portion operable to receive at least a portion of the delivery device. In at least some instances, the pop-up portion may include, in the second configuration, a first inclined guide portion and a second opposing inclined guide portion, the opposing inclined guide portions configured to substantially form a U-shape or a V-shape with respect to the upper surface of the tray portion operable to receive the proximal end of the implant delivery device.

In at least some instances, the receiving portion is operable to receive the implant such that the implant is oriented properly in the implant delivery device. In at least some aspects, the loading apparatus may be configured such that when the implant delivery device is disposed about the at least one inclined guide portion, deposition of the implant onto the delivery device causes the implant to translate down the inclined guide portion towards the receiving portion such that at least a portion of the leading edge of the implant is received into the distal end of the implant delivery device received in the receiving portion. In at least some cases, the receiving portion is operable to receive the implant such that a leading edge of the implant is at least partially received in the receiving portion. In at least some instances, the receiving portion is operable to substantially fix or anchor the implant delivery device while the implant is received at the recessed receiving portion.

According to one aspect of the present disclosure, the receiving portion may take the form of a channel or otherwise comprise a channel. The channel may include at least two opposing walls defining the channel. In some instances, the at least two opposing walls defining the channel may be substantially perpendicular to the upper surface. In such instances, the opposing walls may be substantially vertical. In other instances, the at least two opposing walls defining the channel may be substantially inclined. In such cases, the inclined opposing walls may be characterized by a first angle of inclination that is different from the angle of inclination characteristic of the at least one inclined guide portion. The channel may be a rectangular channel, a circular channel, a conical channel, a polygonal channel, an oval channel, and any combination thereof.

In at least one aspect, the loading apparatus may further include a lip coupled with an upper edge of the wall of the tray portion. The lip may be substantially perpendicular to the wall and/or substantially parallel to the upper surface of the tray portion. The loading apparatus may also include a lid portion operable to engage a portion of the tray portion in order to substantially enclose the reservoir of the tray portion. The lip of the tray portion may be configured to engage with a bottom surface or an edge of the lid portion thereby substantially enclosing the reservoir of the tray portion. In at least some aspects, the lid may be coupled to a handle portion for manipulating the lid. In some instances, the lip may be operable to help fix or anchor the implant delivery device during loading and/or to retain wetting solution during wetting of the implant delivery device.

According to at least one aspect of the present disclosure, systems and kits are provided. The systems and kits may include the loading apparatus according to any embodiment described herein and an implant delivery device operable to deliver an implant into a surgically-created implant pocket in a subject. The kits and systems may include the implant delivery device received in the loading apparatus within the reservoir of the tray portion and sterilely sealed by the lid portion. The kits and systems may further include an implant disposed about the delivery device received in the loading apparatus contained within the reservoir and sterilely sealed by the lid portion.

According to at least one aspect of the present disclosure, a method of loading an implant into an implant delivery device is provided. The method may include providing a loading apparatus having a receiving portion operable to receive at least a portion of the implant delivery device. The loading device may have at least one inclined guide portion. The method may further include providing an implant delivery device having a proximal end operable for receiving the implant during loading and a distal end operable to be contacted with an incision in the subject during delivery of the implant into an implant pocket in the subject. At least a portion of the proximal end of the implant delivery device may be disposed about the at least one inclined guide portion and at least a portion of the distal end of the implant delivery device is received in the receiving portion. The method may further include depositing an implant onto the proximal end, or portion thereof, of the implant delivery device disposed about the at least one inclined guide portion such that the implant is caused to translate down the inclined guide portion towards the receiving portion such that at least a portion of the leading edge of the implant is received into the distal end of the implant delivery device received in the recessed receiving portion.

The loading apparatus employed in the method may further include a pop-up portion operable to deploy from a substantially flat undeployed first configuration to an extended deployed second configuration, the extended second configuration comprising at least one inclined guide portion. In such instances, the method may further include causing the pop-up portion to deploy from a substantially flat undeployed first configuration to an extended deployed second configuration having at least one inclined guide portion. Causing the pop-up portion to deploy may include causing the application of force to one or more push or pull tabs. In at least some instances, the method may include causing the pop-up portion to deploy from a substantially flat undeployed first configuration to an extended deployed second configuration having a plurality of inclined guide portions, the plurality of inclined guide portions arranged in opposition to substantially form a U-shape or a V-shape configured to receive at least a portion of the proximal end of the implant delivery device. The method may further include removing a lid portion enclosing the delivery device disposed in a reservoir of the loading apparatus and unfolding one or more portions of the proximal end of the delivery device in order to prepare the delivery device for receiving the implant.

The method may further include causing the implant delivery device to be placed on the loading device such that at least a portion of the distal end of the implant delivery device is received in the receiving portion and at least a portion of the proximal end of the implant delivery device is disposed about the at least one inclined guide portion. In some instances, the method may include pouring the implant from a sterile bowl onto the implant delivery device disposed about the at least one inclined guide portion. The method may also include pouring the implant from a sterile bowl onto the implant delivery device disposed about the at least one inclined guide portion. The method may also include wetting the implant delivery device by pouring a liquid wetting solution onto the implant delivery device when the implant delivery device is disposed about the loading apparatus, such that the liquid wetting solution drains into the reservoir and/or the receiving portion, the reservoir serving as a reservoir for the liquid wetting solution.

The method may also include depositing an implant onto the upper surface of the delivery member, or portion thereof, of the implant delivery device disposed about the at least one inclined guide portion such that the implant is caused to slide down the at least one inclined guide portion towards the receiving portion such that at least a portion of the leading edge of the implant is received into the proximal end of the shielding member or the inner bore of the shielding member received in the receiving portion. In some aspects, the method may include causing the implant delivery device to be placed on the loading apparatus such that at least a portion of the shielding member of the implant delivery device is received in the receiving portion and at least a portion of the delivery member of the implant delivery device is disposed about the at least one inclined guide portion.

FIGS. 1-20 depicts perspective views of the loading apparatus and its use, according to exemplary embodiments of the present disclosure. In particular, FIG. 1 depicts an isometric view of a loading apparatus 500 for facilitating the loading of an implant 1100 into an implant delivery device 1000, according to an exemplary embodiment of the present disclosure. The loading apparatus 500 may be used, for example, to properly orient an implant 1100 in an implant delivery device 1000 during loading of the implant 1100 into the implant delivery device 1000. In particular, the loading apparatus 500 may be used to cause or ensure that the leading edge 2603 of the implant 1100 is oriented in the implant delivery device 1000 such that it is the leading edge 2603 of the implant 1100 that first enters the implant pocket upon delivery by the implant delivery device 1000. Loading apparatus 500 may also be used to fix or anchor the implant delivery device 1000 during loading of the implant 1100 into or onto the implant delivery device 1000. In particular, the loading apparatus 500 may be used to minimize movement and maintain sterility of the implant delivery device 1000 during loading and placement of the implant 1100 on the delivery device 1000.

Loading apparatus 500 includes a receiving portion 150. The receiving portion 150 is operable to receive at least a portion of the implant delivery device 1000. Any number of implant delivery devices may be used with loading apparatus 500. An example of an implant delivery device 1000 that may be used with loading apparatus 500 is depicted in FIGS. 21-26. However, the implant delivery devices that are within the spirit and scope of the present disclosure are not limited to the example shown in FIGS. 21-26. In general, implant delivery devices 1000 may have a proximal end 1001 operable for receiving the implant 1100 during loading and a distal end 1002 operable to be contacted with an incision in the subject, or in some instances inserted into the incision in the subject, during delivery of the implant 1100 into an implant pocket in the subject. In such instances, the recessed receiving portion 150 is operable to receive at least a portion of the distal end 1002 of the implant delivery device 1000.

Figure 21:
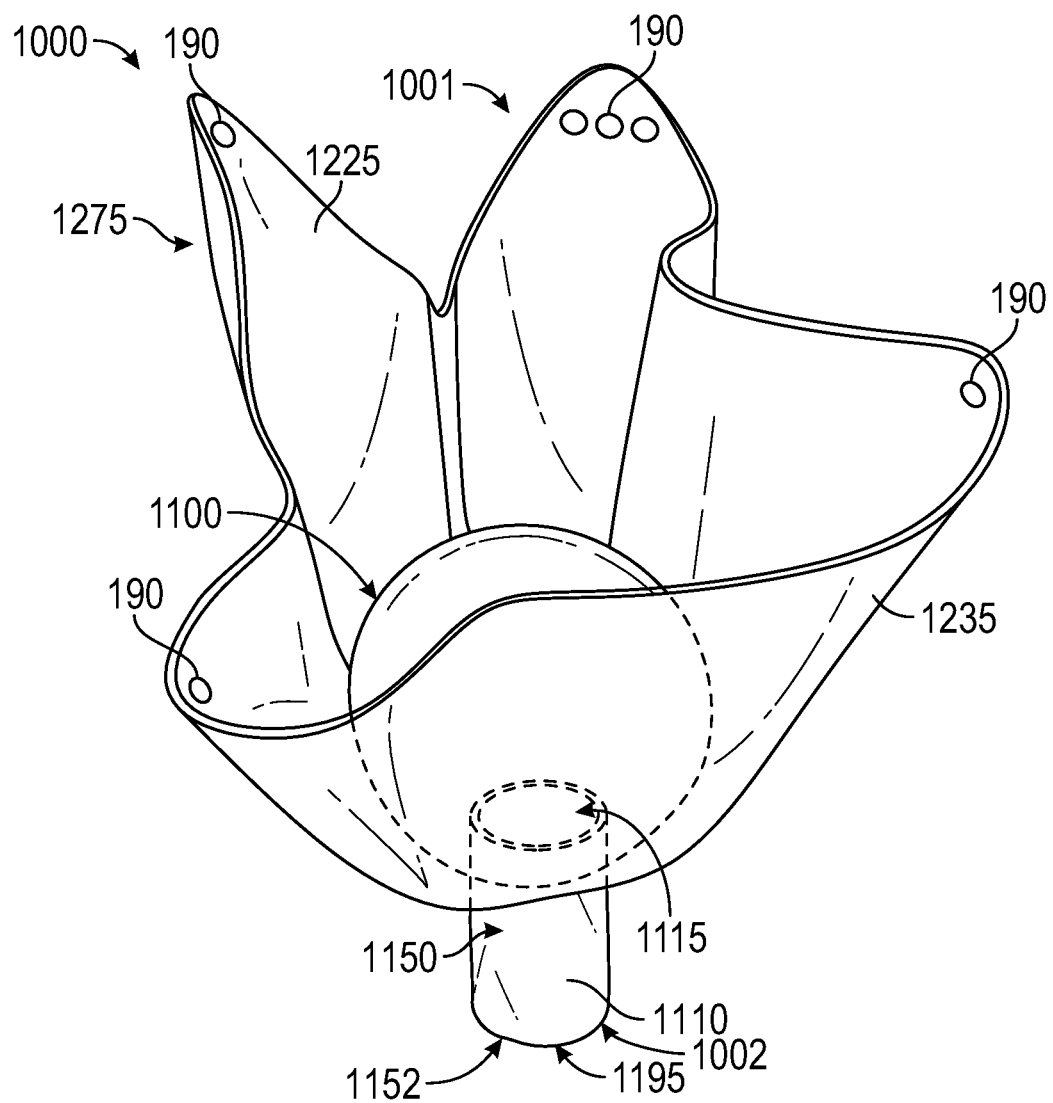
FIG. 21 is a diagrammatic view of the wrapping of the implant in the proximal end or delivery member of the implant delivery device after loading of the implant using the loading device, according to an exemplary embodiment of the present disclosure.

The non-limiting example of the implant delivery device 1000 depicted in FIG. 21 includes a delivery member 1275 having an upper surface 1225 and a lower surface 1235. The implant delivery device 1000 includes an aperture 1220 formed in the delivery member 1275 and extending through the upper surface 1225 and the lower surface 1235. Implant delivery device 1000 further includes a shielding member 1150 coupled with the delivery member 1275. The shielding member 1150 has an inner surface 1105, an outer surface 1110, a proximal end 1151 and a distal end 1152. The proximal end 1151 has a proximal opening 1153 and the distal end 1152 has a distal opening 1154. As depicted in FIG. 21, the proximal end 1151 is coupled with the delivery member 1275 while the distal end 1152 of shielding member 1150 extends away from the delivery member 1275. The shielding member 1150 has an inner bore 1115 defined by inner surface 1105. The outer surface 1110 defines an outer bore 1195 of shielding member 1150 that includes the cross-sectional width of the inner bore 1115 as well as the thickness of the wall of the shielding member 1150 at the particular portion of along the outer surface 1110 that the outer bore 1195 is determined. The distal end 1152 of the shielding member 1150 has an aperture 1155 that is substantially aligned with inner bore 1115 and aperture 1220 of the delivery member 1275 when the shielding member 1150 is extended.

When an implant 1100 is placed on the upper surface 1225 of the delivery member 1275 of the implant delivery device 1000, the delivery member 1275 is operable to wrap around an implant 1100 to form a conforming cavity around the implant 1100 that conforms to the shape of the implant 1100. When the implant 1100 is disposed within the conforming cavity of the implant delivery device 1000, the implant delivery device 1000 is considered loaded and ready to be used to insert the implant 1100 into the surgically-created implant pocket in the subject. The inner bore 1115 of the shielding member 1150 is operable to receive the implant therethrough when mechanical force is applied to the lower surface 1235 of the delivery member 1275, thereby delivering the implant 1100 into a surgically-created implant pocket in a subject.

Figure 10:
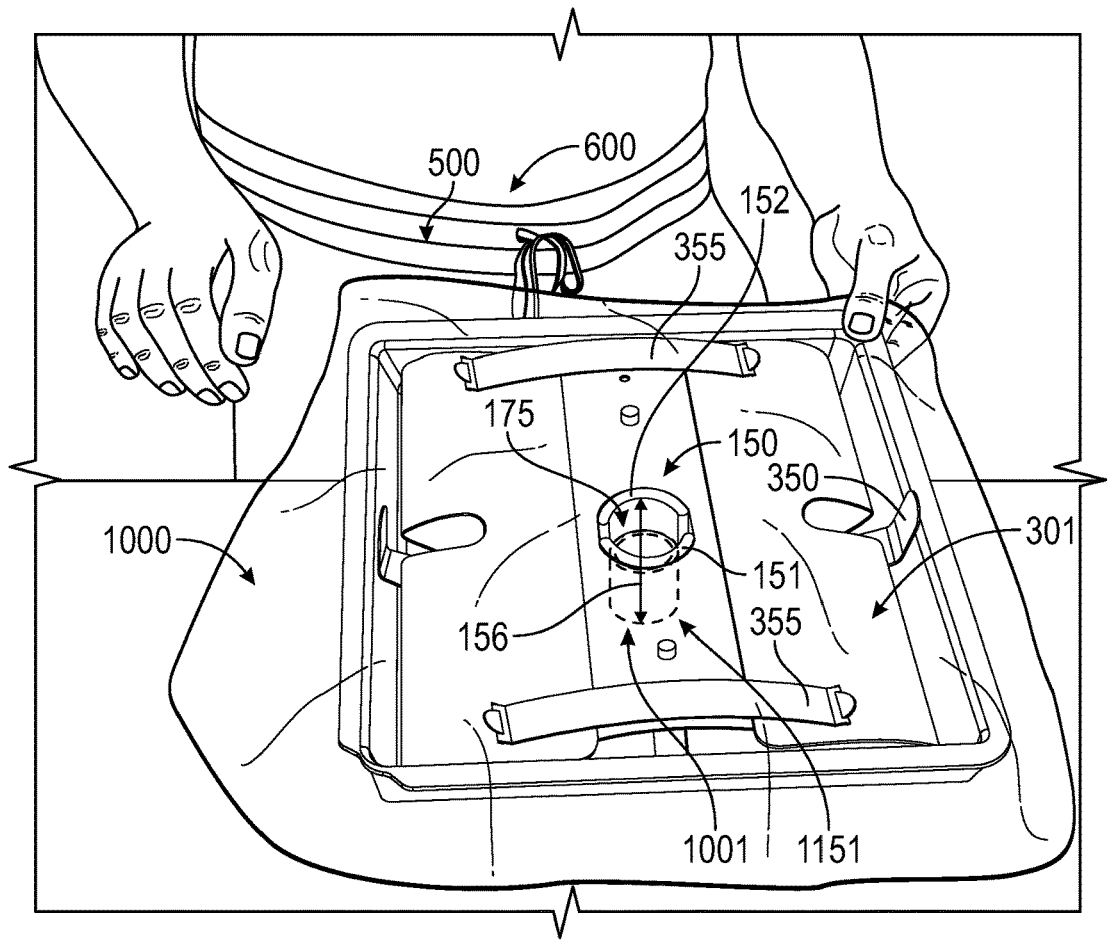
FIG. 10 is an isometric perspective view of a loading apparatus having a pop-up portion in a substantially flat undeployed first configuration and a delivery device received in the receiving portion of the tray portion, with the proximal end of the delivery device unfolded so as to be ready to receive an implant for loading, according to an exemplary embodiment of the present disclosure.
Figure 14:
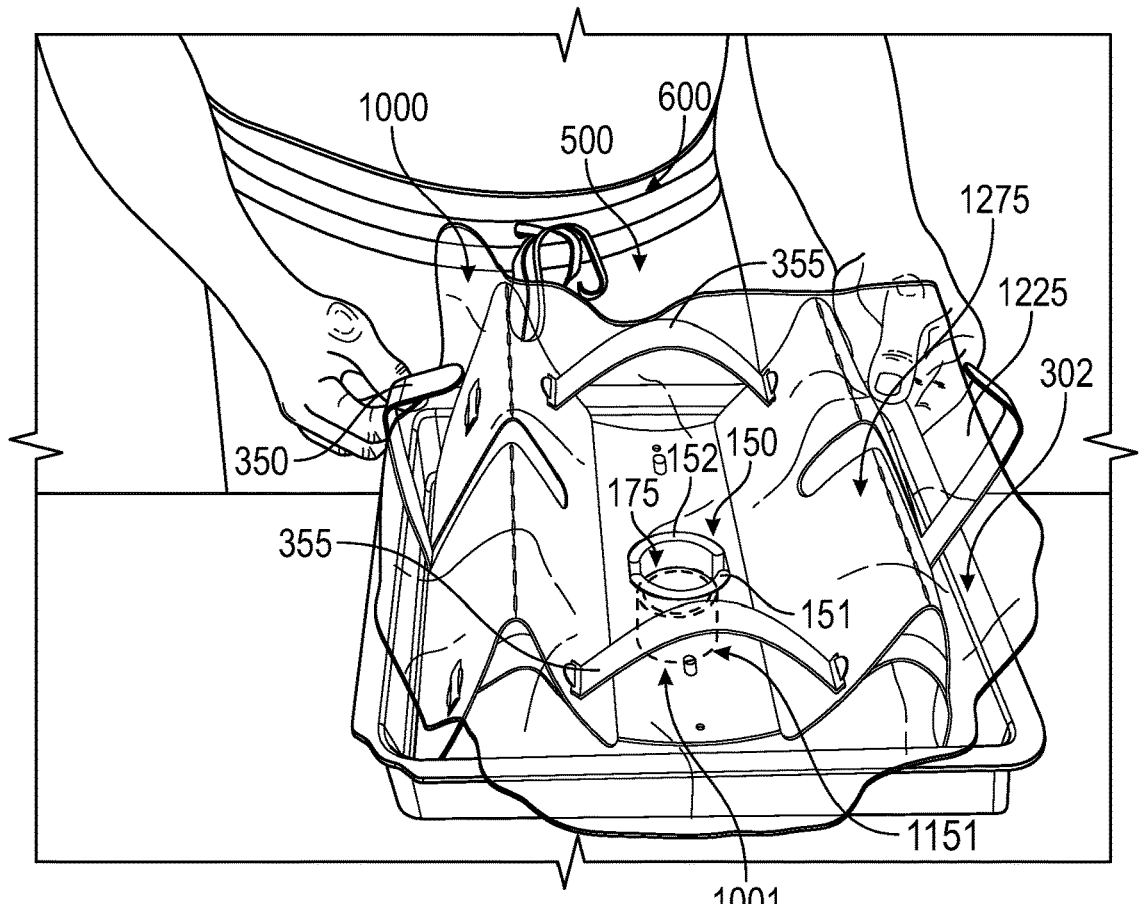
FIG. 14 is an isometric perspective view of a loading apparatus having a pop-up portion in an extended deployed second configuration with the distal end of a delivery received in the receiving portion and a proximal end of the delivery device received on two opposing inclined guide portions and ready to receive an implant for loading, according to an exemplary embodiment of the present disclosure.

Returning to the loading device 500 depicted in FIG. 1, the receiving portion 150 is operable to receive at least a portion of the shielding member 1150 of the implant delivery device 1000, as depicted in FIGS. 10 and 14, showing the inner bore 1115 of shielding member 1150 received in receiving portion 150. In particular, the receiving portion 150 is operable to receive at least a portion of the implant delivery device 1000 such that movement of the implant delivery device 1000 is mitigated during loading of an implant 1100 into the delivery device 1000 or onto a surface of the delivery device 1000. Receiving portion 150 may be particularly configured to receive a distal end 1152 of the implant delivery device 1000. Accordingly, the receiving portion 150 may have a shape that is complementary to the shape of the distal end 1152 of the implant delivery device 1000 so that the receiving portion 150 is configured to receive a distal end 1152 of the implant delivery device 1000.

During loading of the implant 1100 onto implant delivery device 1000, receiving portion 150 may be operable to positionally fix or stabilize the implant delivery device 1000 when the implant delivery device 1000 or a portion thereof is received in the receiving portion 150. Accordingly, the receiving portion 150 is operable to resist or arrest movement of the implant delivery device 1000 during loading when the implant delivery device 1000 or a portion thereof is received in the receiving portion 150.

As depicted in FIG. 1, loading apparatus 500 may further include a tray portion 100 having an upper surface 120, a lower surface 125, an outer edge 205 extending around the upper and lower surfaces, and a wall 210 extending around the outer edge 205 such that the wall 210, together with the upper surface 120, forms a reservoir 250. In some instances, the receiving portion 150 may extend from the upper surface 120 of the tray portion 100, as depicted in FIG. 1. In other embodiments, the pop-up portion 300 discussed below may comprise the receiving portion 150. The receiving portion 150 is generally located substantially near the center of the upper surface 120 of the tray portion 100. The receiving portion 150 may include one or more walls, such as walls 151,152 depicted in FIG. 1. The two opposing walls 151, 152 may be substantially perpendicular to the upper surface 120 of the tray portion 100 or may be substantially inclined to upper surface 120 of the tray portion 100. The one or more walls may form a cavity or channel 175 operable to receive the distal end 1152 of the implant delivery device 1000, or a portion thereof. In some cases, the one or more walls 151 may form a recessed receiving portion 150 operable to receive the distal end of the implant delivery device 1000, or a portion thereof, therein. In the exemplary embodiment shown in FIG. 1, receiving portion 150 comprises a channel 175 or cavity formed by opposing walls 151, 152. However, in some embodiments the receiving portion 150 may not include a channel but may instead comprise any mechanism capable of retaining or receiving a distal end or portion of the delivery device 100. One of skill in the art will recognize that delivery devices 100 may vary and therefore the structure and mechanism of receiving portion 150 may likewise vary so long as it performs the function described in the present disclosure. For example, in some instances, the receiving portion 150 may comprise a friction fit component, a clip, a sleeve, or similar device or means for receiving or retaining the implant delivery device.

In some instances, the receiving portion 150 may comprise a retaining ring 225. In such instances, the retaining ring 225 may be under tension such that when the implant delivery device 1000 or a portion thereof is received in the receiving portion 150 with the tension being operable to resist movement of the implant delivery device 1000 during loading. The tension may be generated by one or more springs. In such instances, the receiving portion 150 comprises a spring-loaded retaining ring.

Figure 5:
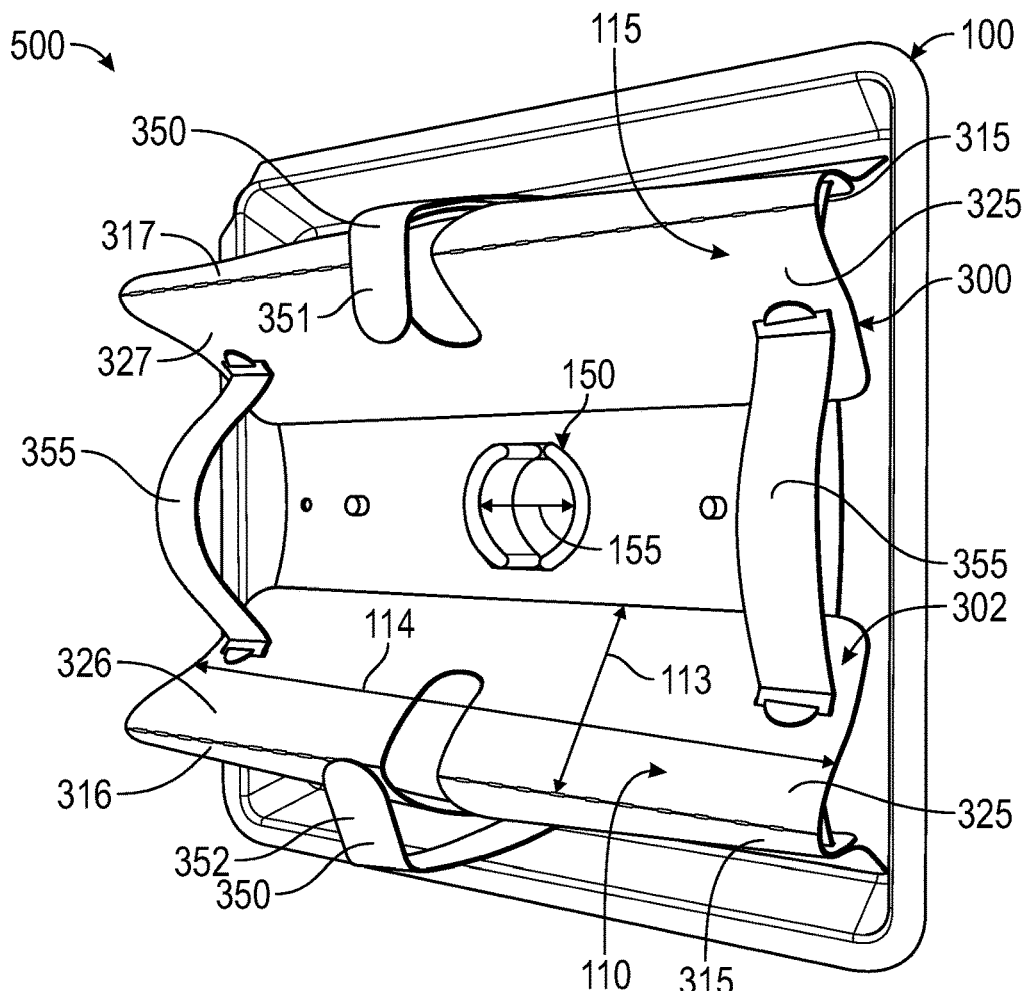
FIG. 5 is a top perspective view of a loading apparatus having a pop-up portion with two elevatable members in an extended deployed second configuration, according to an exemplary embodiment of the present disclosure.
Figure 6:
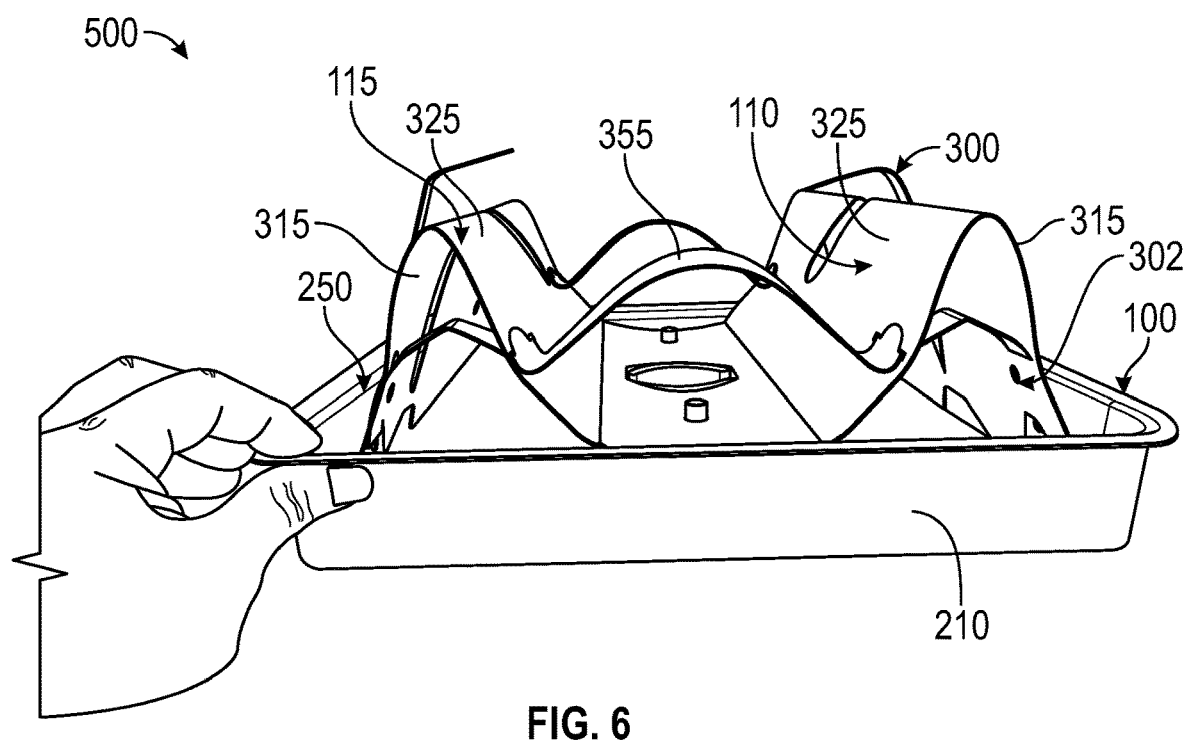
FIG. 6 is a side perspective view of a loading apparatus having a pop-up portion with two elevatable members in an extended deployed second configuration, according to an exemplary embodiment of the present disclosure.
Figure 7:
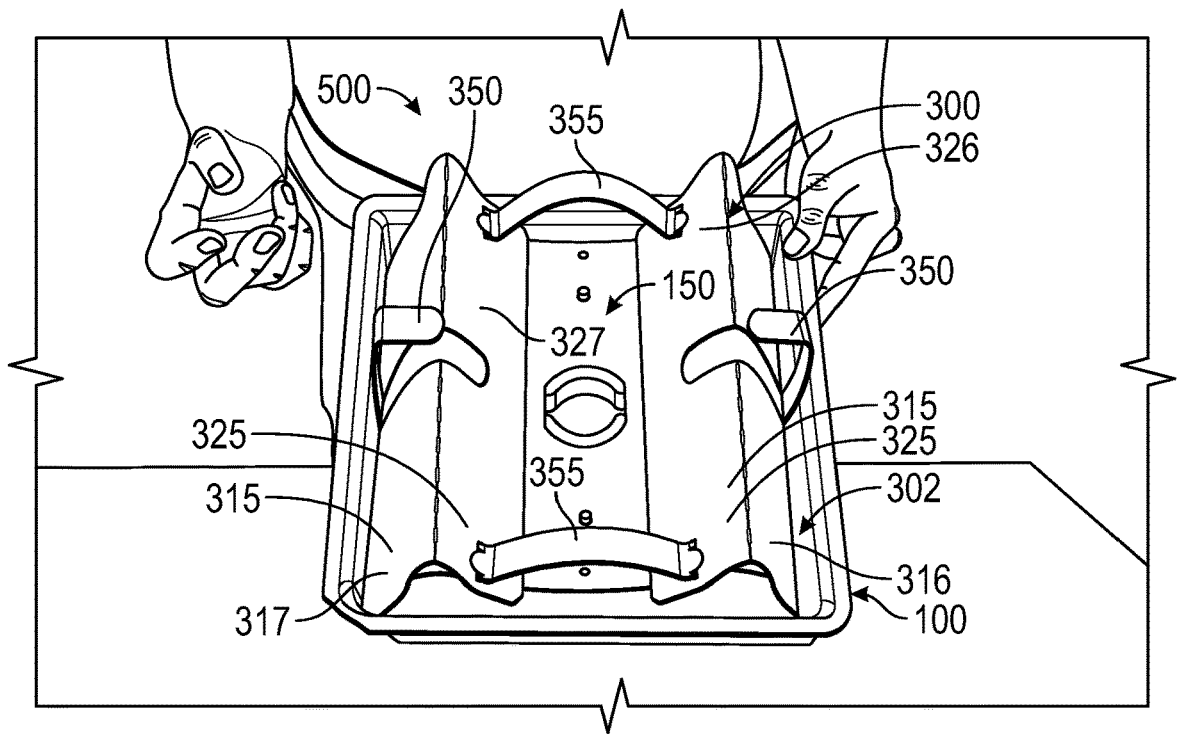
FIG. 7 is an isometric perspective view of a loading apparatus having a pop-up portion with two elevatable members in an extended deployed second configuration ready to receive a delivery device, according to an exemplary embodiment of the present disclosure.

As depicted in FIG. 1, loading apparatus may further include a pop-up portion 300 operable to deploy from a substantially flat undeployed first configuration 301 to an extended deployed second configuration 302. The extended second configuration 302 includes at least one inclined guide portion 110. The pop-up portion 300 includes an extendable member 315 and an elevatable member 325, as shown in FIG. 1. The extendable member 315 is coupled to the elevatable member 325 such that when the extendable member 315 is extended, the elevatable member 325 is elevated to form at least one inclined guide portion 110. The non-limiting embodiment shown in FIG. 1 depicts a first extendable member 316 coupled to a first elevatable member 326 and a second extendable member 317 coupled to a second elevatable member 327. The pop-up portion 300 is operable such that when the first and second extendable members 316, 317 are extended, the first and second elevatable members 326, 327 are elevated to each form an inclined guide portion 110 and an opposing inclined guide portion 115, respectively, such that the inclined guide portion and the opposing inclined guide portions substantially form a U-shape or a V-shape with respect to the upper surface 120 of the tray portion 100, as shown in FIGS. 5-7.

Figure 2:
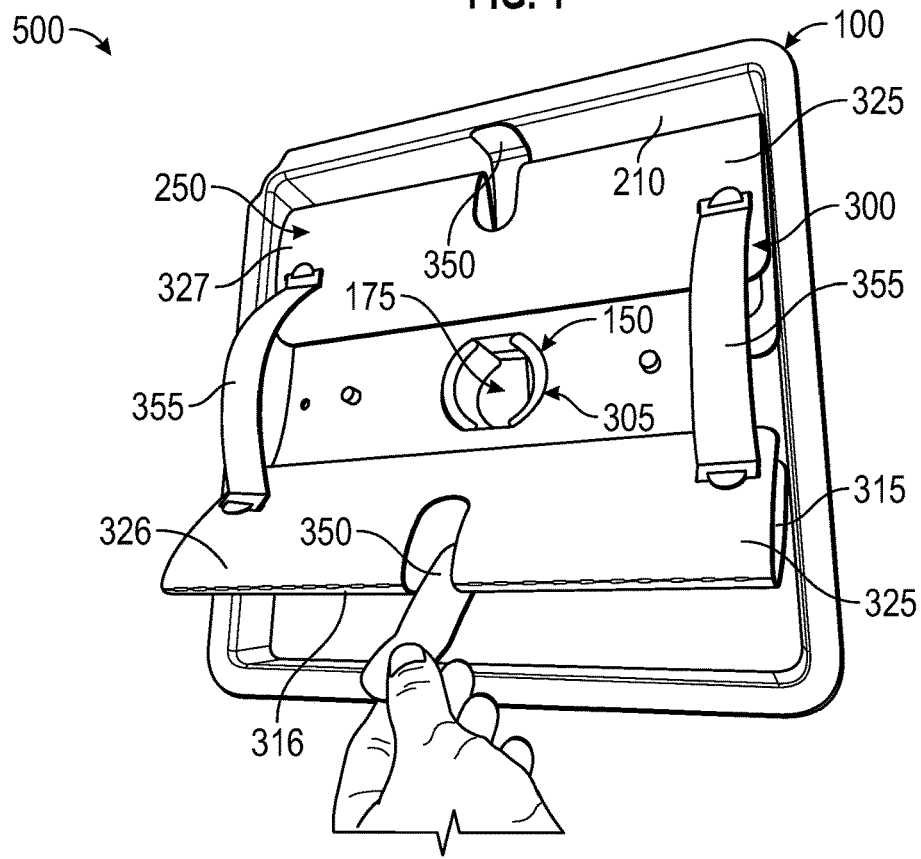
FIG. 2 is a top perspective view of a loading apparatus having a pop-up portion in a partially deployed configuration, according to an exemplary embodiment of the present disclosure.
Figure 3:
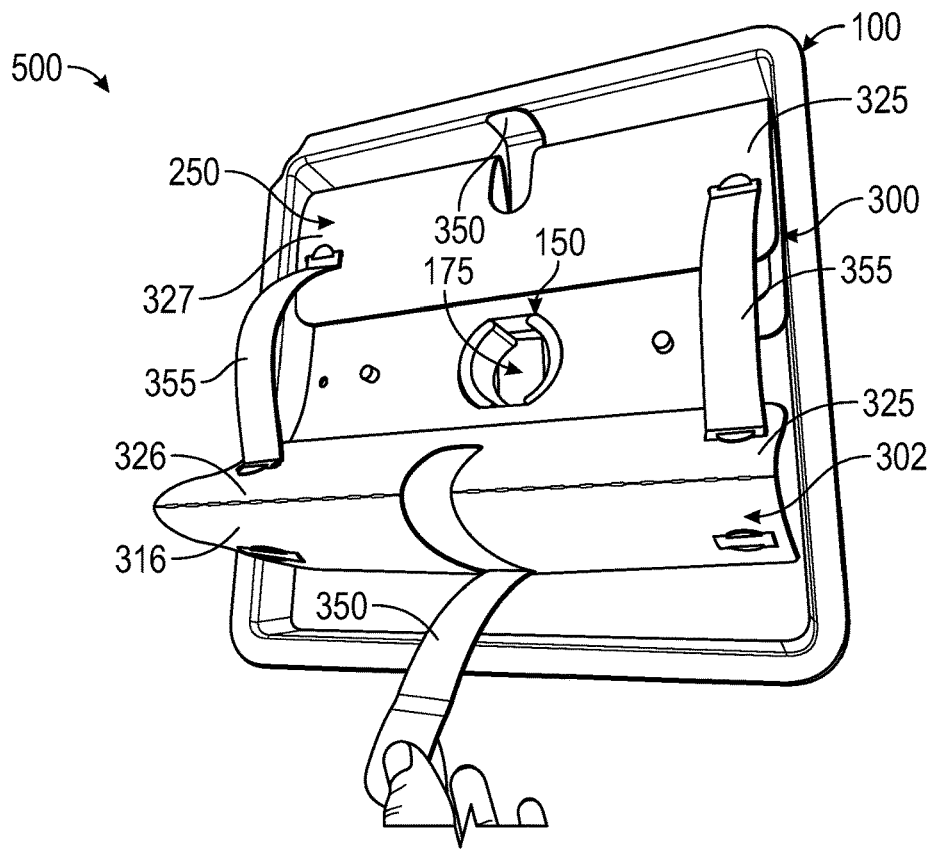
FIG. 3 is a top perspective view of a loading apparatus having a pop-up portion in a partially deployed configuration, according to an exemplary embodiment of the present disclosure.
Figure 4:
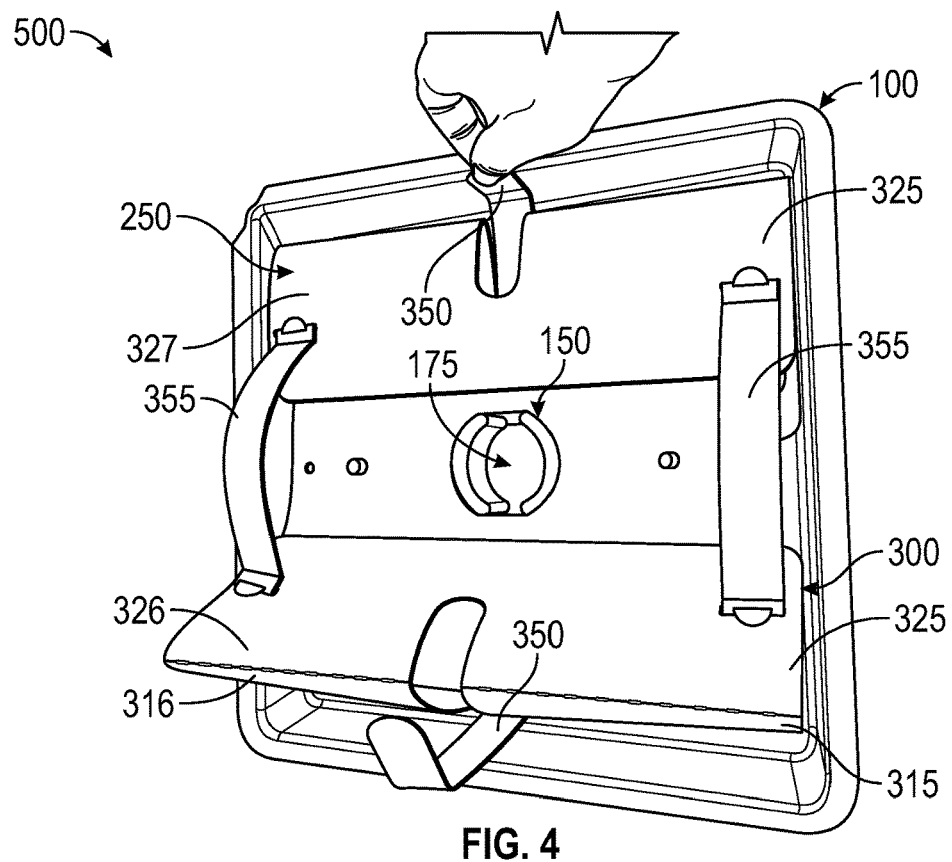
FIG. 4 is a top perspective view of a loading apparatus having a pop-up portion with a first elevatable member in a deployed second configuration comprising a first inclined guide portion and second elevatable member in a substantially flat undeployed first configuration, according to an exemplary embodiment of the present disclosure.

As shown in FIGS. 2-4, pop-up portion 300 may include one or more push or pull tabs 350 coupled to the extendable member 315 such that the extendable member 315 is configured to extend upon application of force to the push or pull tab 350. The one or more push or pull tabs 350 may be integrally formed from one or more of the extendable members 315. The one or more push or pull tabs 350 may be formed from the same material that constitutes the one or more extendable members 315. As shown in FIGS. 2-4, the pop-up portion 300 is operable to deploy from the undeployed substantially flat first configuration 301 to the deployed extended second configuration 302 upon the application of force to the push or pull tab 350. The tray portion 300 may be configured such that the travel of the extendable member 315 during extension is limited by contact with an opposing wall 210 of the tray portion 100, as shown in FIGS. 5-6. The pop-up portion 300 may further include one or more travel limiters 355. The one or more travel limiters 355 may couple the first elevatable member 326 to the second elevatable 327 thereby limiting travel or inclination of the first and second elevatable members during extension of the first and second extendable members 316, 317, as shown in FIGS. 6-7.

In some embodiments, the pop-portion 300 may comprise the receiving portion 150. In such instances, the receiving portion 150 is generally located substantially near the center of pop-up portion 300. As depicted in FIGS. 1-7, pop-up portion 300 includes aperture 305 configured to receive the receiving portion 150 on the tray portion 100 such that the distal end 1152 of implant delivery device 100 may be received in receiving portion 150 while the proximal end 1151 of implant delivery device is disposed about the pop-up portion 100. In such instances, the receiving portion 150 of tray portion 100 may be coupled to the pop-up portion 300 at aperture 305.

Pop-up portion 300 is operable to be retained within the reservoir 250 of the tray portion 100. In particular, pop-up portion 300 may be secured to tray portion 100 by one or more retaining mechanisms 380 operable to couple the pop-up portion 300 to the tray portion 100 so that at least a portion of the pop-up portion 300 is anchored to the tray portion 100 during loading of the delivery device 1000 with implant 1100. The one or more retaining mechanisms 380 are also operable to couple the pop-up portion 300 to the tray portion 100 so that at least a portion of the pop-up portion 300 is retained in the reservoir 250 of the tray portion 100 during deployment of the pop-up portion 300 from the first configuration 301 to the second configuration 302. In some embodiments, the retaining mechanism 380 may be a retaining pin or a retaining clip.

Figure 8:
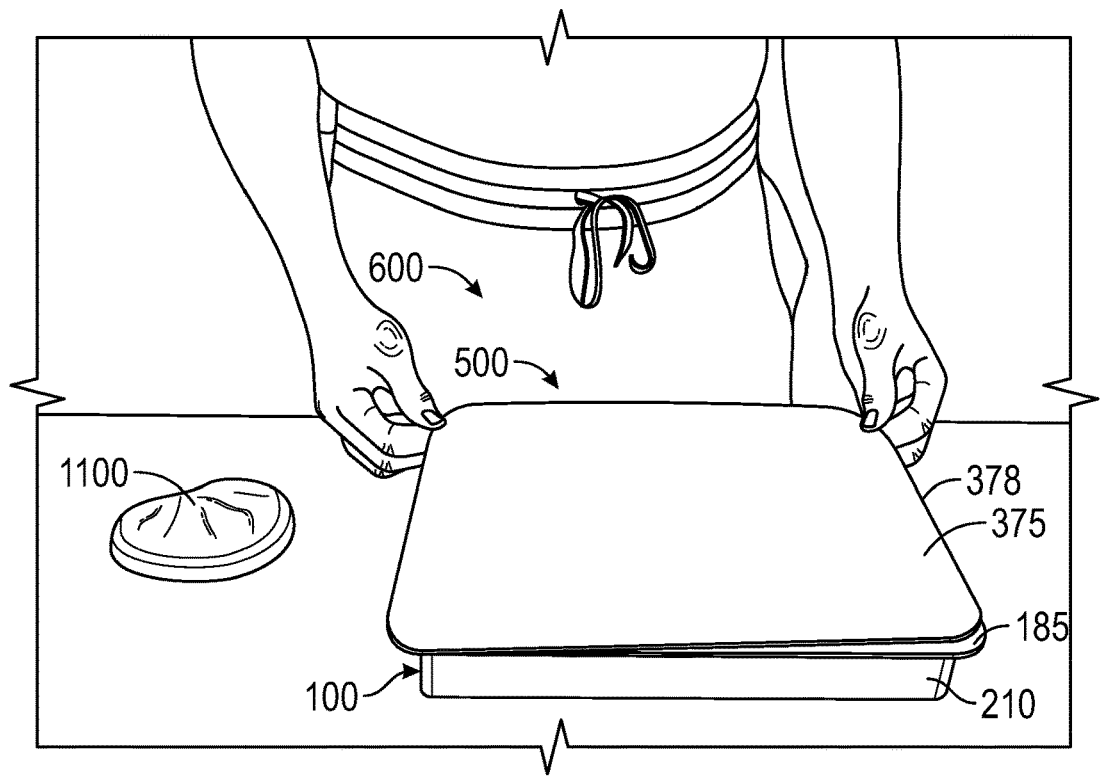
FIG. 8 is an isometric perspective view of a loading system and loading apparatus having a lid portion operable to enclose the delivery device and the pop-up portion within the tray portion of the system and apparatus, according to an exemplary embodiment of the present disclosure.
Figure 9:
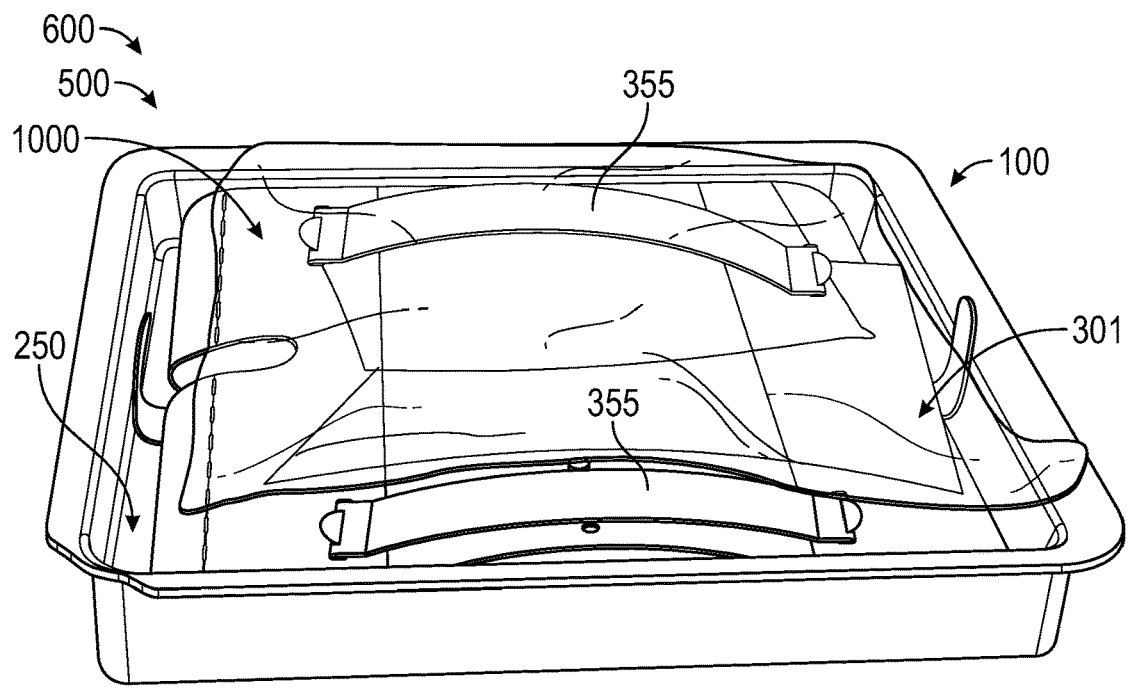
FIG. 9 is an isometric perspective view of a loading apparatus having a pop-up portion in a substantially flat undeployed first configuration and a delivery device received in the receiving portion of the tray portion, according to an exemplary embodiment of the present disclosure.

According to at least one aspect, the loading apparatus 500, system 600, and kit may be packaged and shipped in a sealed package comprising the tray portion 100 containing the pop-up portion 300 and implant delivery device 1000. In particular, the pop-up portion 300 and implant delivery device 1000 may be disposed in the reservoir 250 of tray portion 100 and enclosed by a lid portion 375, as shown in FIGS. 8 and 9. The lid portion 375 may be operable to engage a portion of the tray portion 100 in order to substantially enclose the reservoir 250 of the tray portion 100. Tray portion 100 may include a lip 185 coupled with an upper edge of the wall 210 of the tray portion 100. The lip 185 may be substantially perpendicular to the wall 210 and/or substantially parallel to the upper surface 120 of the tray portion 100. The lip 185 of the tray portion 100 may be configured to engage with a bottom surface 377 or an edge 378 of the lid portion 375 thereby substantially enclosing the reservoir 250 of the tray portion 100. In at least some aspects, the lid portion 375 may be coupled to a handle portion for manipulating the lid portion 375. In some instances, the lip 185 may be operable to help fix or anchor the implant delivery device 1000 during loading and/or to retain wetting solution during wetting of the implant delivery device 1000.

Figure 11:
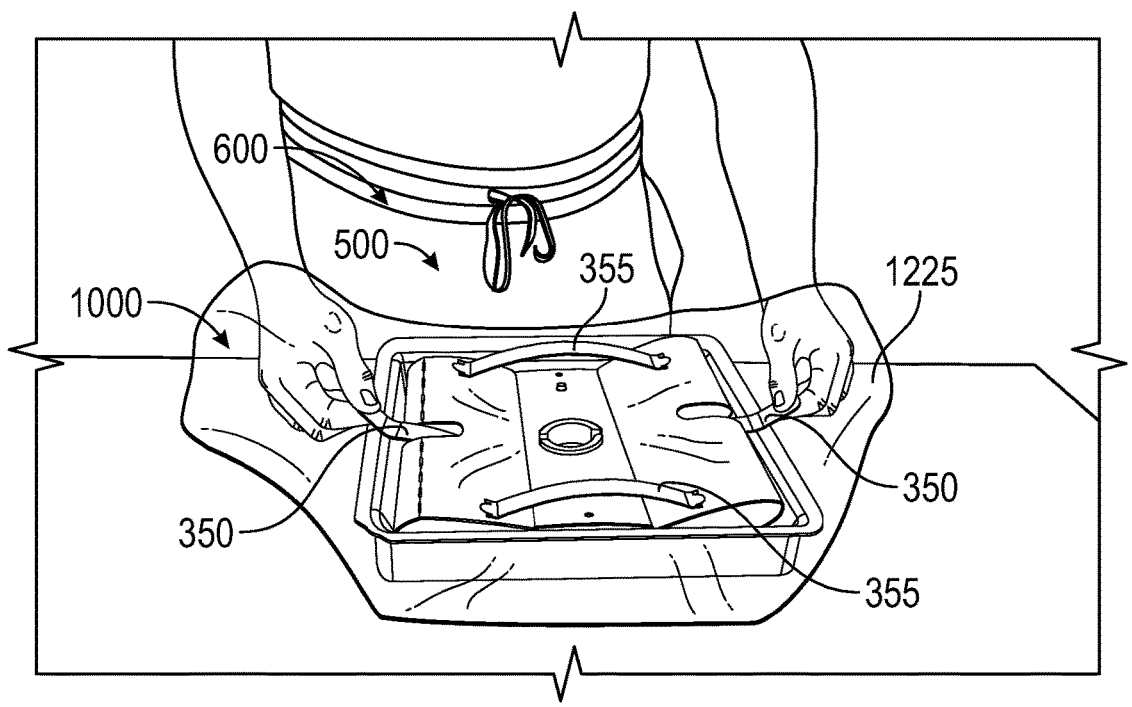
FIG. 11 is an isometric perspective view of a loading apparatus having a pop-up portion being deployed from a substantially flat undeployed first configuration to an extended deployed second configuration by application of force to a plurality of push or pull tabs, according to an exemplary embodiment of the present disclosure.
Figure 12:
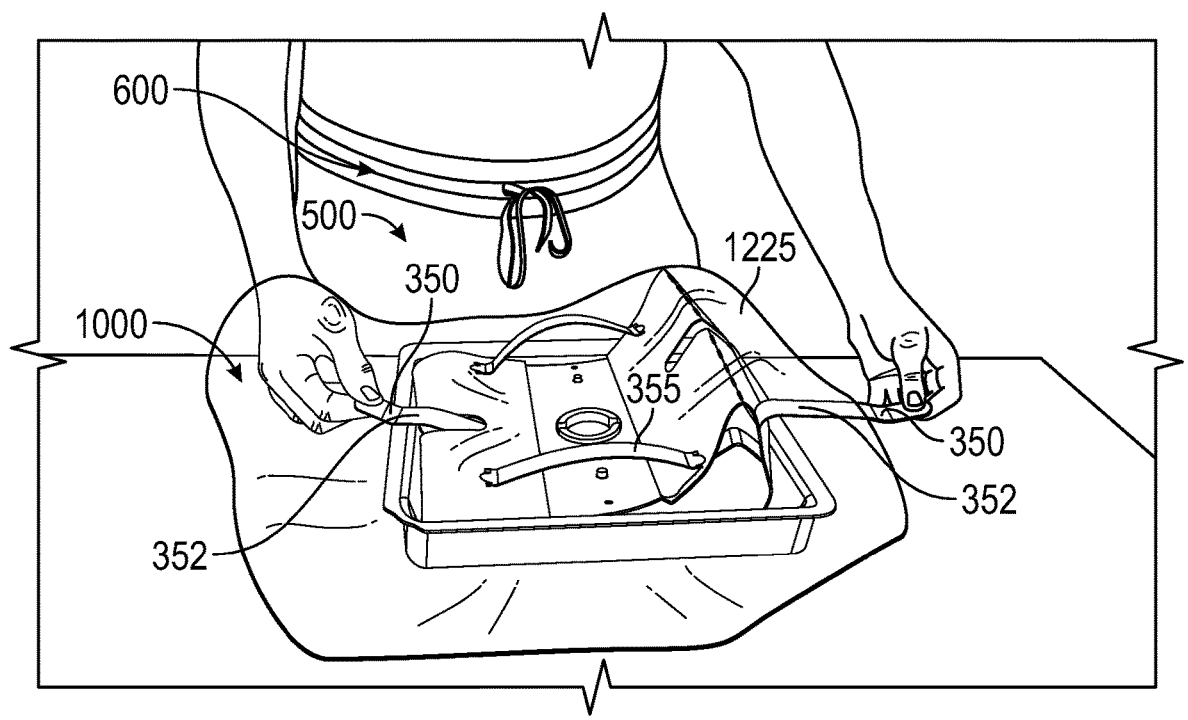
FIG. 12 is an isometric perspective view of a loading apparatus having a pop-up portion being deployed from a substantially flat undeployed first configuration to an extended deployed second configuration by application of force to a plurality of push or pull tabs, according to an exemplary embodiment of the present disclosure.

Prior to deployment of the pop-up portion 300, the implant delivery device 1000 may be disposed about an upper surface of elevatable member 325 which is substantially parallel to the upper surface 120 of tray portion 1000, as shown in FIGS. 9-11. As shown in FIG. 1, when the pop-up portion 300 is in the undeployed first configuration 301, the extendable member 315 is folded beneath the elevatable member 325. Reservoir 250 is operable to completely contain the pop-up portion 300 when the pop-up portion is in the substantially flat undeployed first configuration 301. As shown in FIGS. 9 and 10, the proximal end 1151 of delivery device 1000 may be folded during shipment and unfolded by a user in order to prepare the implant delivery device 1000 for receiving the implant 1100.

Figure 16:
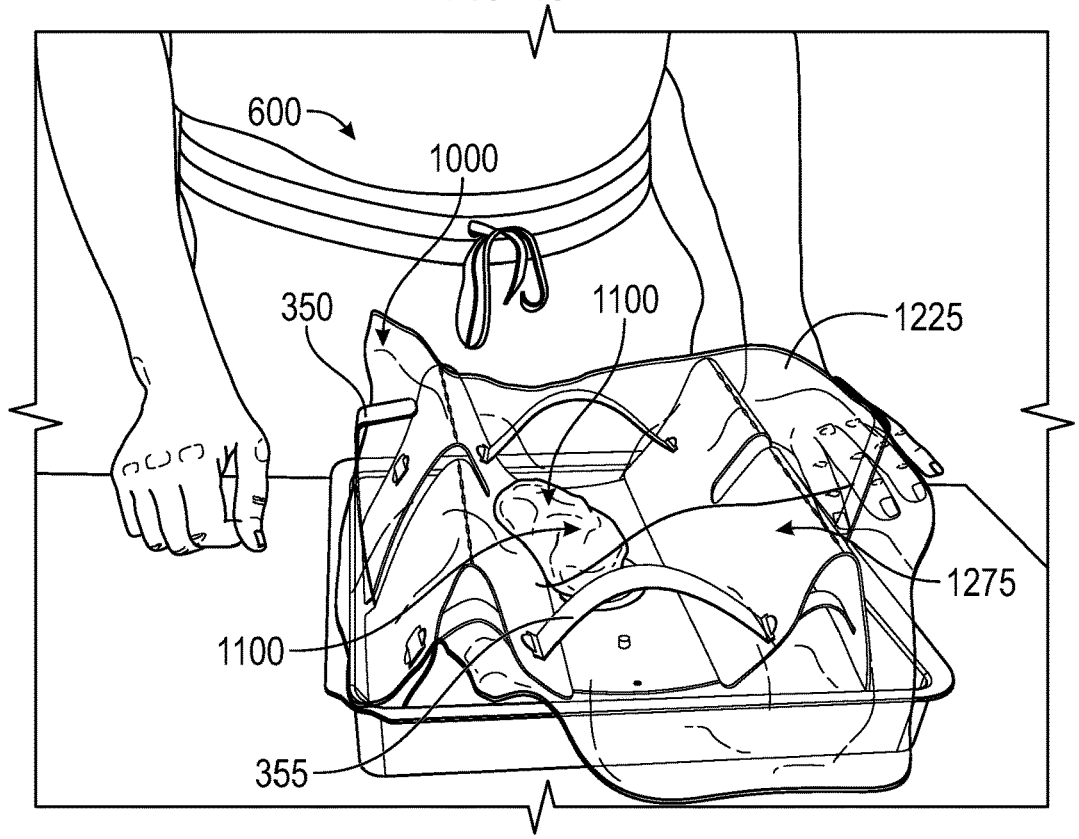
FIG. 16 is an isometric perspective view of an implant deposited on a delivery device received in the loading apparatus with the leading edge of the implant at least partially received in the distal end of the delivery device received in the receiving portion, according to an exemplary embodiment of the present disclosure.

Before the implant 1100 is deposited on implant delivery device 1000 disposed about pop-up portion 300 and received in receiving portion 150, the pop-up portion 300 must be deployed from the substantially flat first configuration 301 to the extended second configuration 302 comprising one or more inclined guide portions 110, as shown in FIGS. 11-14. As shown in FIGS. 11-14, the pop-up portion 300 is deployed to the second configuration 302 comprising a first inclined guide portion 110 and opposing guide portion 115 by the application of force to push or pull tabs 350. Implant 1100 may then be deposited onto the proximal end 1151, or portion thereof, of the implant delivery device 1000 disposed about the at least one inclined guide portion 110 such that the implant is caused to translate down the inclined guide portion 110 towards the receiving portion 150 such that at least a portion of the leading edge of the implant 1100 is received into the distal end 1152 of the implant delivery device 1000 received in the receiving portion 150, as shown in FIG. 16. In some instances, depositing the implant 1100 onto the delivery member 1000 may include pouring the implant from a sterile bowl onto the implant delivery device 1000 disposed about the at least one inclined guide portion 110.

Once the implant 1100 is correctly oriented in delivery device 1000, the implant delivery device 1000 or a portion thereof may be wrapped around the implant 1100 in order to load the implant delivery device 1000 with the implant 1100, as shown in FIGS. 17-20.

Loading apparatus 500 may include any number of inclined guide portions 110. For example, loading apparatus 500 may include, one (1) inclined guide portion, two (2) inclined guide portions, three (3) inclined guide portions, four (4) inclined guide portions, five (5) inclined guide portions, six (6) inclined guide portions, or any other number of inclined guide portions. The inclined guide portion 110 may be any shape so long as it is operable to guide the implant as described in the present disclosure. For example, the inclined guide portion 110 may have or otherwise include an inclined ramp, a conical surface, a curvilinear surface, a curved surface, a trapezoidal surface, and any combination thereof.

Tray portion 100 may be constructed of or formed from any suitable material including a plastic polymer, PVC, vinyl, or any combination thereof. As depicted in FIGS. 1-20, tray portion 100 includes a rectangular tray 100, however, tray portion 100 may be any shape.

The at least one inclined guide portion 110 may also have a first length 113 and a second length 114. The first length 113 may be from about 2 cm to about 15 cm, or from about 4 cm to about 5 cm, or from about 6 cm to about 7 cm, or from about 4 cm to about 12 cm, or from about 4 cm to about 10 cm, or from about 4 cm to about 7 cm. The second length 114 may be from about 8 cm to about 20 cm, or from about 8 cm to about 17 cm, or from about 7 cm to about cm, or from about 7 cm to about 35 cm, or from about 8 cm to about 15 cm, or from about 8 cm to about 12 cm.

In at least some instances, the recessed portion 150 may take the form of a channel or otherwise comprise a channel, such as channel 175 depicted in FIGS. 1-20. As shown in FIG. 1, channel 175 may include at least two opposing walls defining the channel 175, such as opposing walls 151, 152 depicted in FIGS. 1-20. As depicted in FIGS. 1-20, the at least two opposing walls 151, 152 defining the channel may be substantially perpendicular to the lower surface and/or substantially perpendicular to the upper surface. In such instances, the opposing walls 151, 152 may be substantially vertical. In other instances, the at least two opposing walls defining the channel may be substantially inclined. In such cases, the inclined opposing walls may be characterized by a first angle of inclination that is different from the angle of inclination characteristic of the at least one inclined guide portion.

The channel 175 may be any shaped channel so long as it operable as described in the present disclosure. For example, channel 175 may be a rectangular channel, a circular channel, a conical channel, a polygonal channel, an ellipsoid channel, and any combination thereof. In particular, channel 175 may be any shape or dimension so long as it is operable to cause the leading edge 2603 of the implant 1100 to be received in the inner bore 1115 of shielding member 1150 after being guided toward the recessed receiving portion 150 by the guide portion 110. In at least some instances, the channel 175 is sized and shaped such that only the leading edge 2603 of the implant 1100 is oriented such that it is facing the distal end 1002 of the implant delivery device 1000 after being guided toward the recessed receiving portion 150 by the guide portion 110.

FIGS. 10 and 14 depict the loading apparatus 500 having an implant delivery device 1000, or at least a portion thereof, received in bowl 105. In particular, the distal end 1002 of the implant delivery device 1000, including the inner bore 1115 of shielding member 1150, is received in the channel 175 of recessed receiving portion 150. Additionally, at least a portion of the proximal end 1001 of the implant delivery device 1000, including delivery member 1275, is disposed about the at least one inclined guide portion 110. As depicted in FIGS. 10 and 14, the at least one inclined guide portion 110 engages the lower surface 1235 of delivery member 1275 such that the upper surface 1225 of delivery member 1275 is operable to receive an implant 1100 thereon.

In at least some instances, it may be advantageous for a surgeon to wet the delivery device 1000 and/or the implant 1100 with a liquid wetting solution so that the delivery device is more easily wrapped around the implant and/or inserted into the incision and such that the implant 1100 may be more easily delivered to the surgically-created implant pocket in the subject. In such instances, the recessed receiving portion 150 and reservoir 250 are operable to serve as a reservoir for receiving and retaining a liquid wetting solution for wetting the delivery device. Additionally, the at least one inclined guide portion 110 is operable to direct the liquid wetting solution to the receiving portion 150 and reservoir 250 so that it may be retained in the loading apparatus 500 without interfering with the loading and/or orienting of the implant 1100 into the delivery device 1000. In at least some instances, the at least one inclined guide portion 110 is in fluid communication with the receiving portion 150 and reservoir 250 of tray portion 100.

Figure 15:
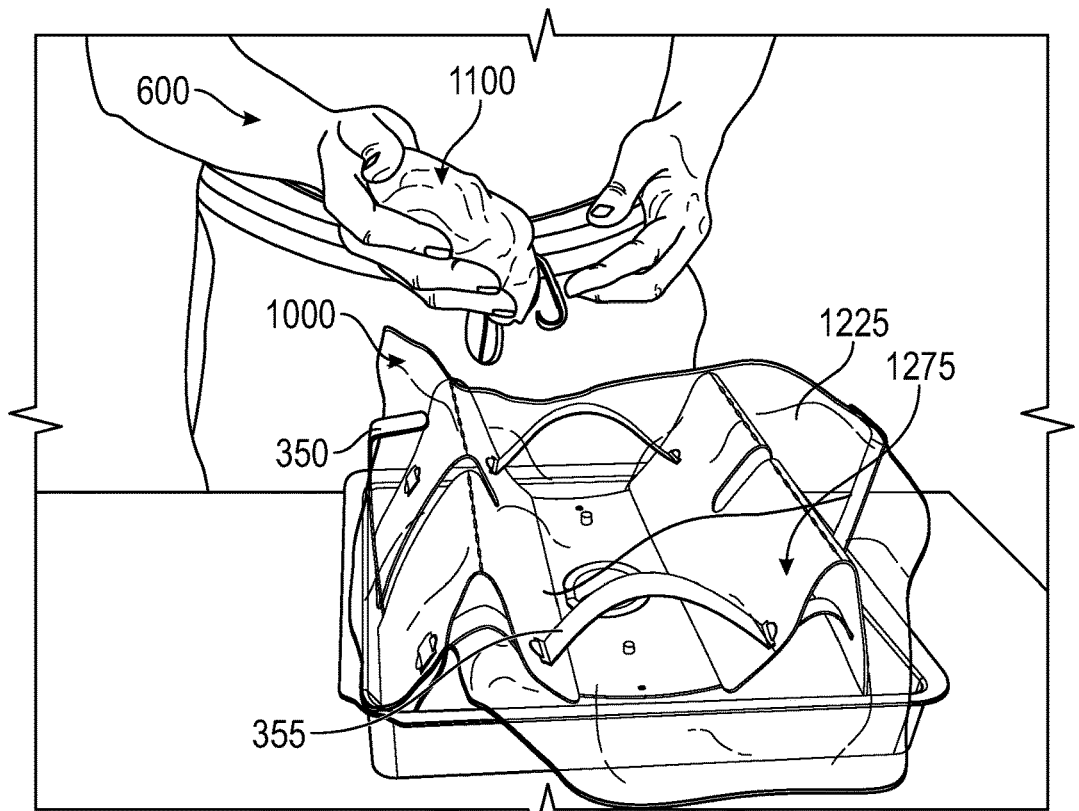
FIG. 15 is an isometric perspective view of an implant being deposited on a delivery device received in the loading apparatus, according to an exemplary embodiment of the present disclosure.

As shown in FIGS. 15 and 16, sterile implant 1100 may be deposited on implant delivery device 1000. In some instances, sterile implant 1100 may be poured from its sterile packaging, onto the proximal end 1001 of implant delivery device 1000 and particularly onto the upper surface 1225 of delivery member 1275 such that the implant 1100 may slide or glide down the at least one inclined guide portion 110 until the leading edge 2603 of the implant 1100 is at least partially received in the distal end 1002 and/or the inner bore 1115 of the shielding member 1150 of the implant delivery device 1000, as shown in FIG. 16. Accordingly, when the delivery device 1000 or portion thereof is received in the recessed receiving portion 150, the at least one guide portion 110 is operable to receive the implant 1100 and guide it toward the receiving portion 150 such that at least a portion of the implant 1100 is received in the implant delivery device 1000, or portion thereof, received in the receiving portion 150. In at least some instances, the implant 1100 is lubricated in order to facilitate the glidingly guiding of the implant 1100 down the guide portion 110 towards the receiving portion 150. In addition to correctly orienting the implant 1100 in delivery device 1000, the use of loading apparatus 150 allows for loading of delivery device 1000 without handling the implant 1100 by simply pouring the implant 1100 from its sterile packaging onto the delivery device 1000 received in tray portion 100 of loading apparatus 500.

Figure 27:
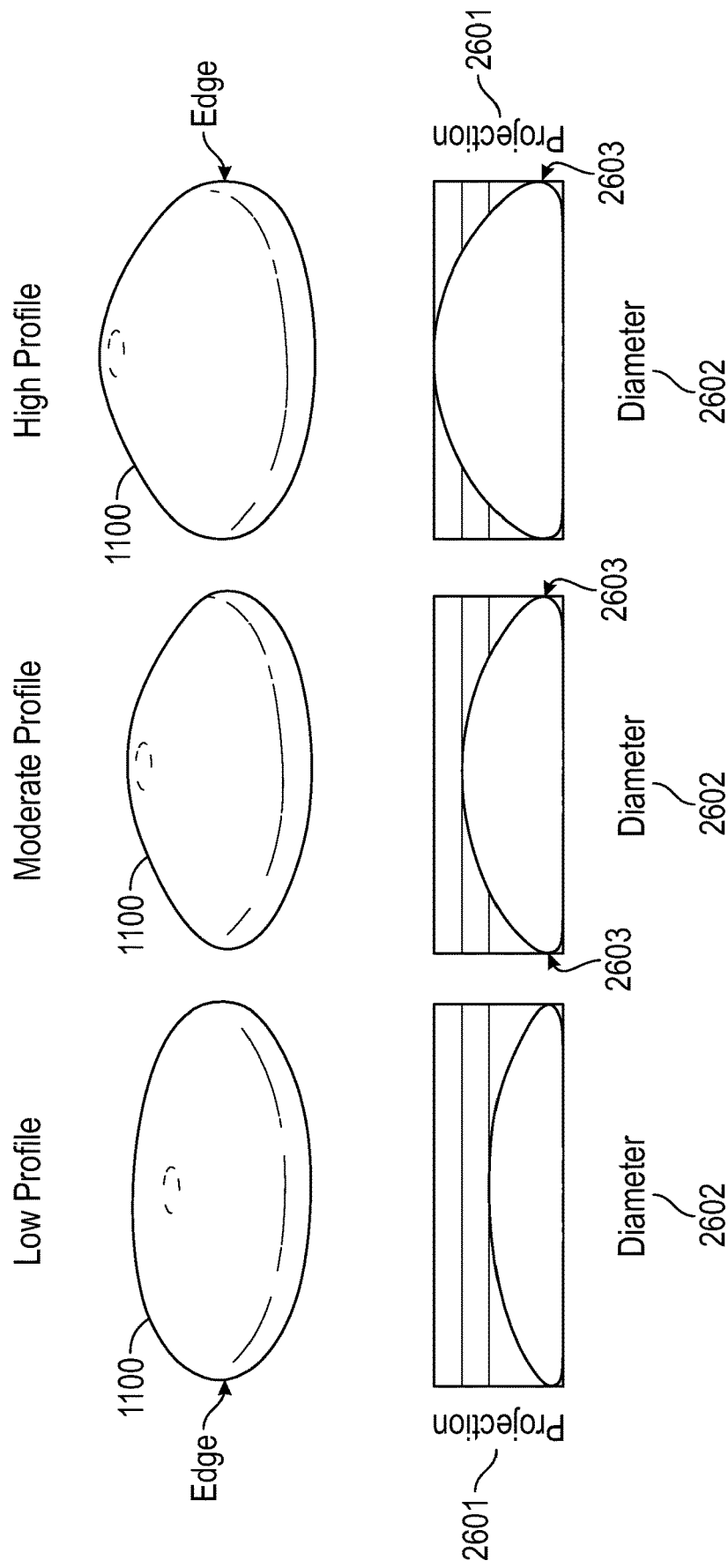
FIG. 27 is a schematic representation of different-shaped implants, each of which are dimensionally characterized by a projection length or axis as well as a diameter length or axis, according to an exemplary embodiment of the present disclosure.

The implant 1100 is characterized dimensionally by a projection 2601 and diameter 2602, as shown in FIG. 27. In order to be correctly positioned in delivery device 1000, the edge 2603 of the implant 1100 must first enter the distal end of the delivery device 1000 and/or the inner bore 1115 of shielding member 1150. According to at least one aspect of the present disclosure, the recessed receiving portion 150 and the channel 175 thereof are sized such that only the leading edge 2603 of the implant 1100 is oriented to be facing the distal end 1002 of the implant delivery device 1000 or to be received in the inner bore 1115 of shielding member 1150 after being guided toward the recessed receiving portion 150 by the guide portion 110. In some instances, the shape and dimensions of the recessed receiving portion 150 and channel 175 therein is such that the recessed receiving portion 150 and channel 175 operate to only permit the leading edge 2603 of the implant 1100 to first enter the recessed receiving portion 150, as well as the distal end 1002 and/or shielding member 1150 disposed in the recessed receiving portion 150, so that the implant is oriented correctly in the implant delivery device 1000.

In at least some instances, the recessed receiving portion 150 may comprise a channel 175 having a cross-sectional width 155 that is greater than the projection (e.g., height) of the implant 1100. In some instances, the recessed receiving portion 150 and/or channel 175 may have a cross-sectional width 155 that is less than the diameter of the implant 1100. In at least some cases, the recessed receiving portion 150 and/or channel 175 may have a length 157 that is greater than the diameter of the implant. In some cases, the channel 175 may have a cross-sectional width 155 that is from about 2 cm to about 7 cm. The channel 175 may also have a depth 156 of from about 1 cm to about 10 cm.

By receiving the distal end 1002 and/or shielding member 1150 of the delivery device 1000 into the recessed receiving portion 150, the loading device 100 and recessed receiving portion 150 is operable to substantially fix or anchor the implant delivery device 1000 while the implant 1100 is poured onto the inclined guide portion 110 as well as while the implant 1100 is guided toward the recessed receiving portion 150 to be received in distal end 1002 and/or inner bore 1115 of shielding member 1150 with the correct orientation. As described throughout the present disclosure, the recessed receiving portion 150 is also operable to receive the implant 1100 such that the implant is oriented properly in the implant delivery device including such that a leading edge 2603 of the implant is at least partially received in the recessed receiving portion 150.

Figure 17:
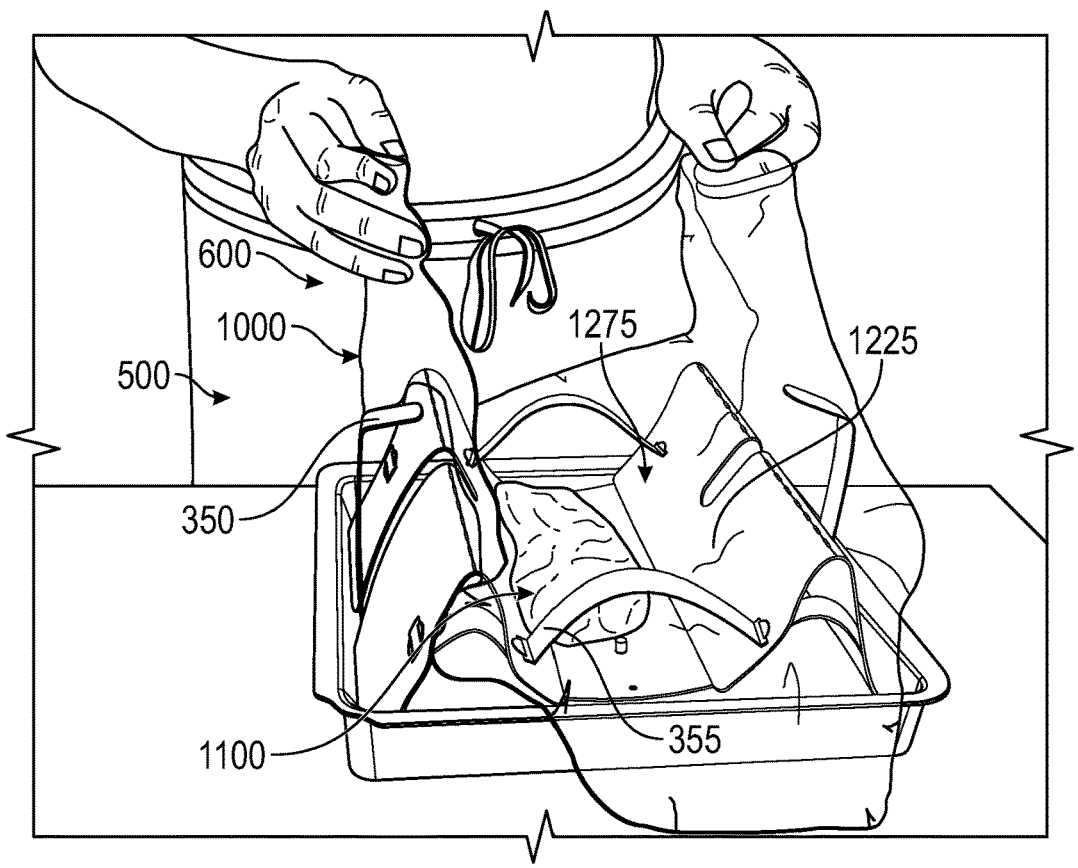
FIG. 17 is an isometric perspective view of an implant being wrapped in a delivery device after being properly oriented in the delivery device using the loading apparatus, according to an exemplary embodiment of the present disclosure.
Figure 18:
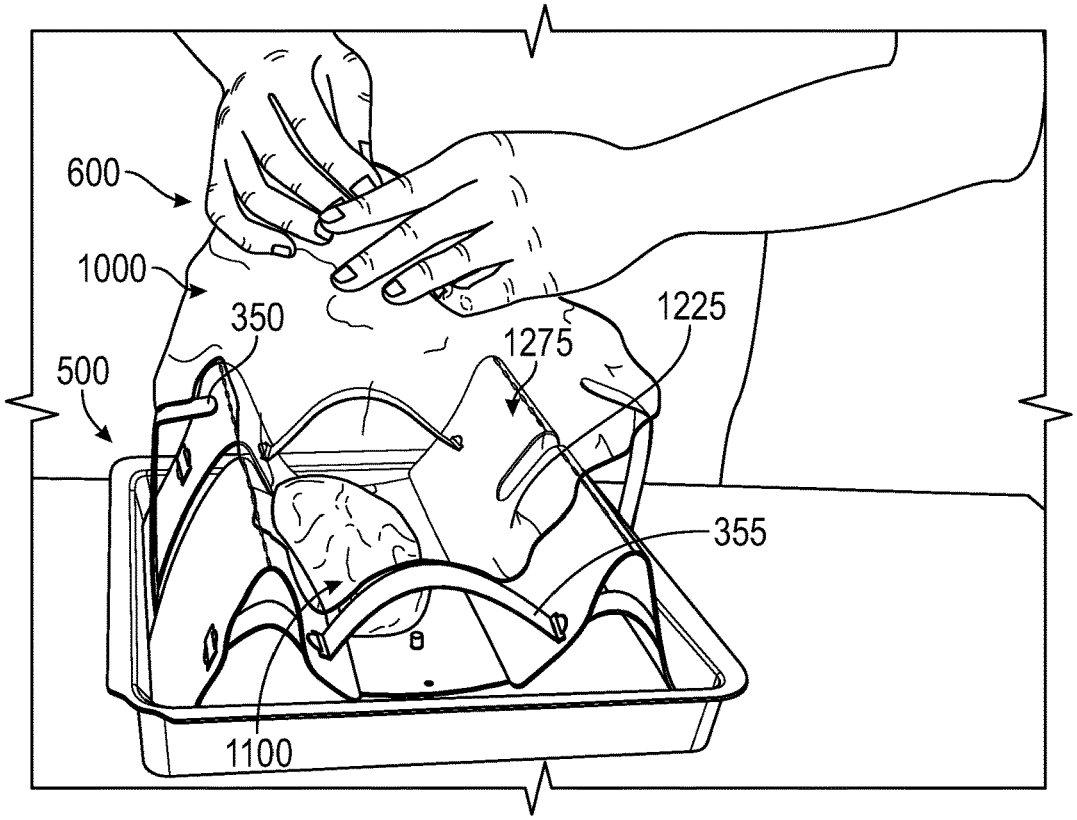
FIG. 18 is an isometric perspective view of an implant being wrapped in a delivery device after being properly oriented in the delivery device using the loading apparatus, according to an exemplary embodiment of the present disclosure.
Figure 19:
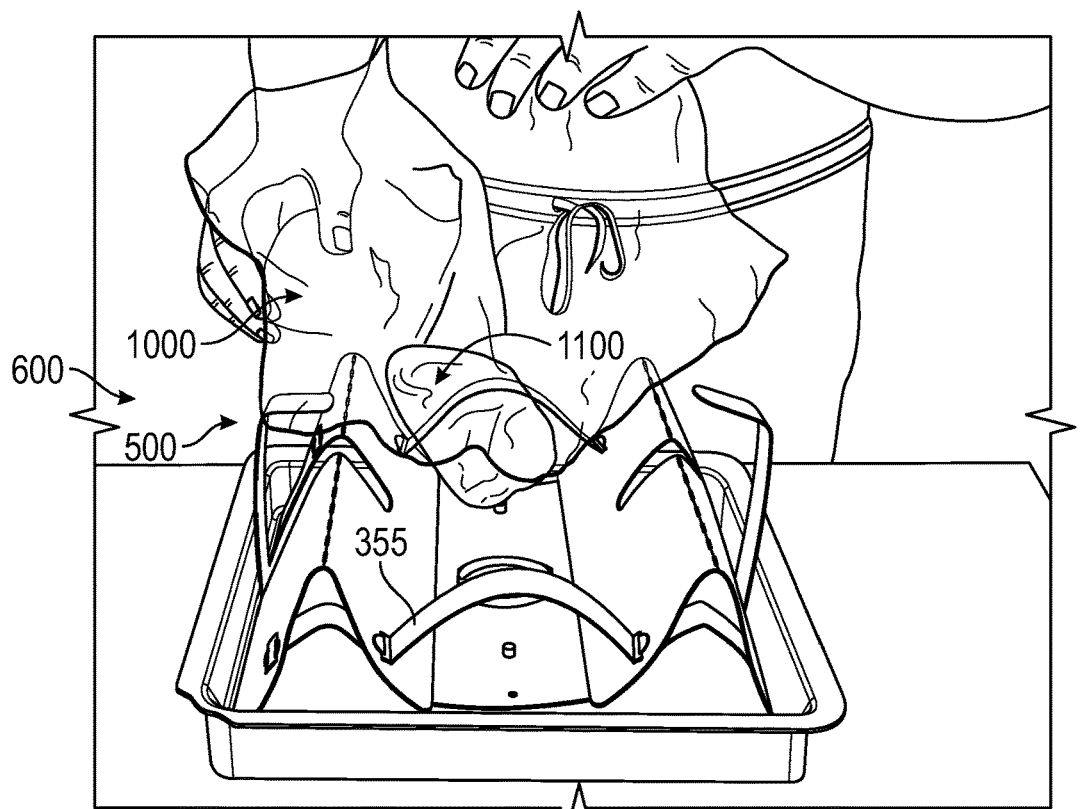
FIG. 19 is an isometric perspective view of an implant being wrapped in a delivery device after being properly oriented in the delivery device using the loading apparatus, according to an exemplary embodiment of the present disclosure.
Figure 20:
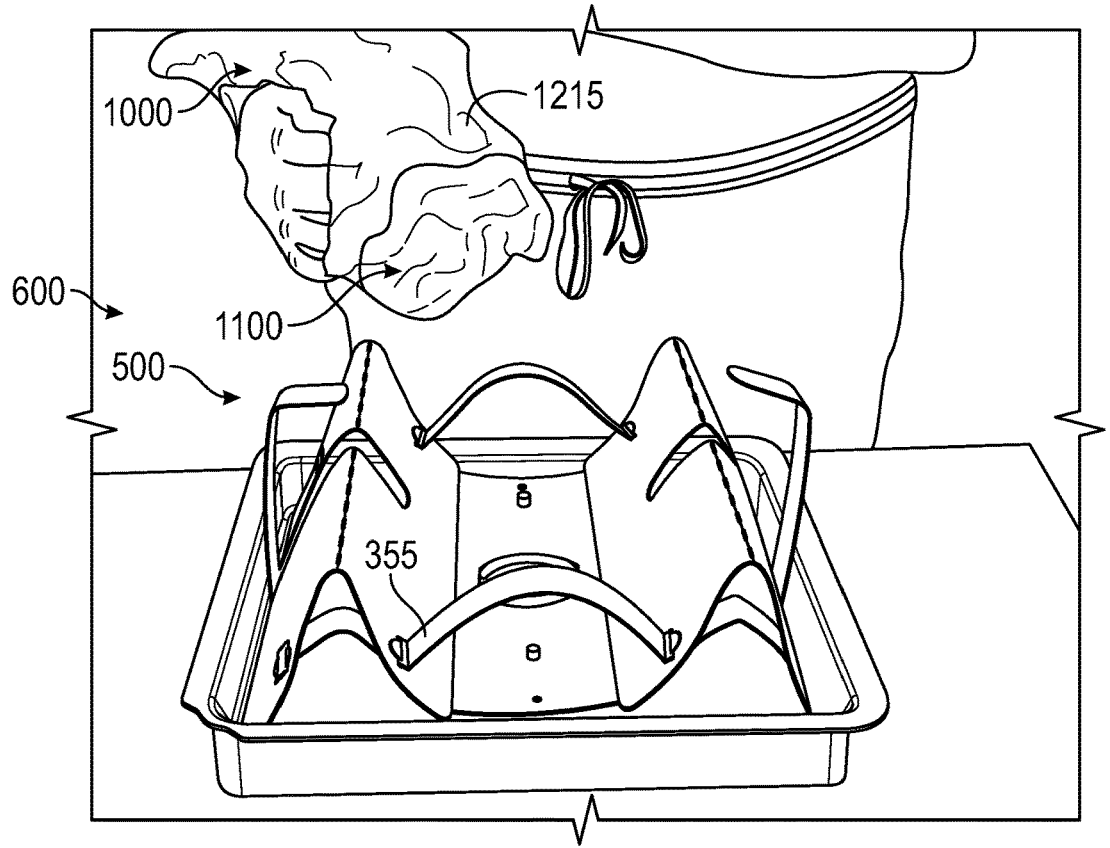
FIG. 20 is an isometric perspective view of an implant being wrapped in a delivery device after being properly oriented in the delivery device using the loading apparatus, according to an exemplary embodiment of the present disclosure.

Once the leading edge 2603 of the implant 1100 is at least partially received in the recessed receiving portion 150 and properly oriented or positioned in the distal end 1002 and/or shielding member 1150 of the delivery device 1000, the proximal end 1001 and/or the delivery member 1275 may be wrapped around the implant 1100 to generate a loaded delivery device as shown in FIGS. 17-20. In particular, once the implant 1100 is poured into bowl 105 and the leading edge 2603 of the implant 1100 is properly received in the inner bore 1115 of the shielding member 1150 of implant delivery device 1000 as shown in FIGS. 16 and 17, the four corners of the proximal end 1001 of the implant delivery device 1000 may be brought together towards opposing portions of the proximal end 1001 so that a conforming pocket is formed around the implant 1100, as shown in FIGS. 17-20.

As shown in FIGS. 21-26, the proximal end 1001 and/or delivery member 1275 of delivery device 1000 may include a plurality of fasteners 190. The plurality of fasteners 190 may be spaced apart along the proximal end 1001 of the delivery device 1000 such that one or more opposing fasteners 190 may be fastened or secured so as to prevent gross movement of the implant during handling of the loaded implant delivery device 1000 prior to insertion of the implant 1100 into the implant pocket of the subject. As depicted in FIGS. 21-26, the fasteners may be arranged in at least two arrangements. In a first arrangement, at least four fasteners may be spaced equidistantly along the proximal end 1001 of the delivery device 1000 so that two pairs of opposing fasteners may be fastened thereby securing the loaded implant 1100 into the implant delivery device 1000. In a second arrangement, one fastener may be positioned on at least three of the four opposing portions of the proximal end 1001, with the fourth opposing portion having three fasteners operable to be fastened to each of the fasteners disposed on each of the other three opposing portions, as shown in FIGS. 21-26.

The fasteners 190 are an optional feature and are not necessary for the functioning of the devices described herein. The fasteners 190 prevent gross movement of the implant 1100 in loaded delivery device during handling and allow the surgeon to place the loaded delivery device down on a surgical table prior to insertion of the implant into the implant pocket in the subject. Engagement of the fasteners 190 are not necessary for the mechanical insertion of the implant 1100 into the implant pocket from the implant delivery device 1000. The fasteners 190 also do not create a seal in the proximal end of the implant delivery device 1000 and do not seal the implant into the delivery device 1000. Air and fluid may pass from the conforming cavity surrounding the implant 1100 even if the fasteners 190 are engaged or fastened.

Figure 23:
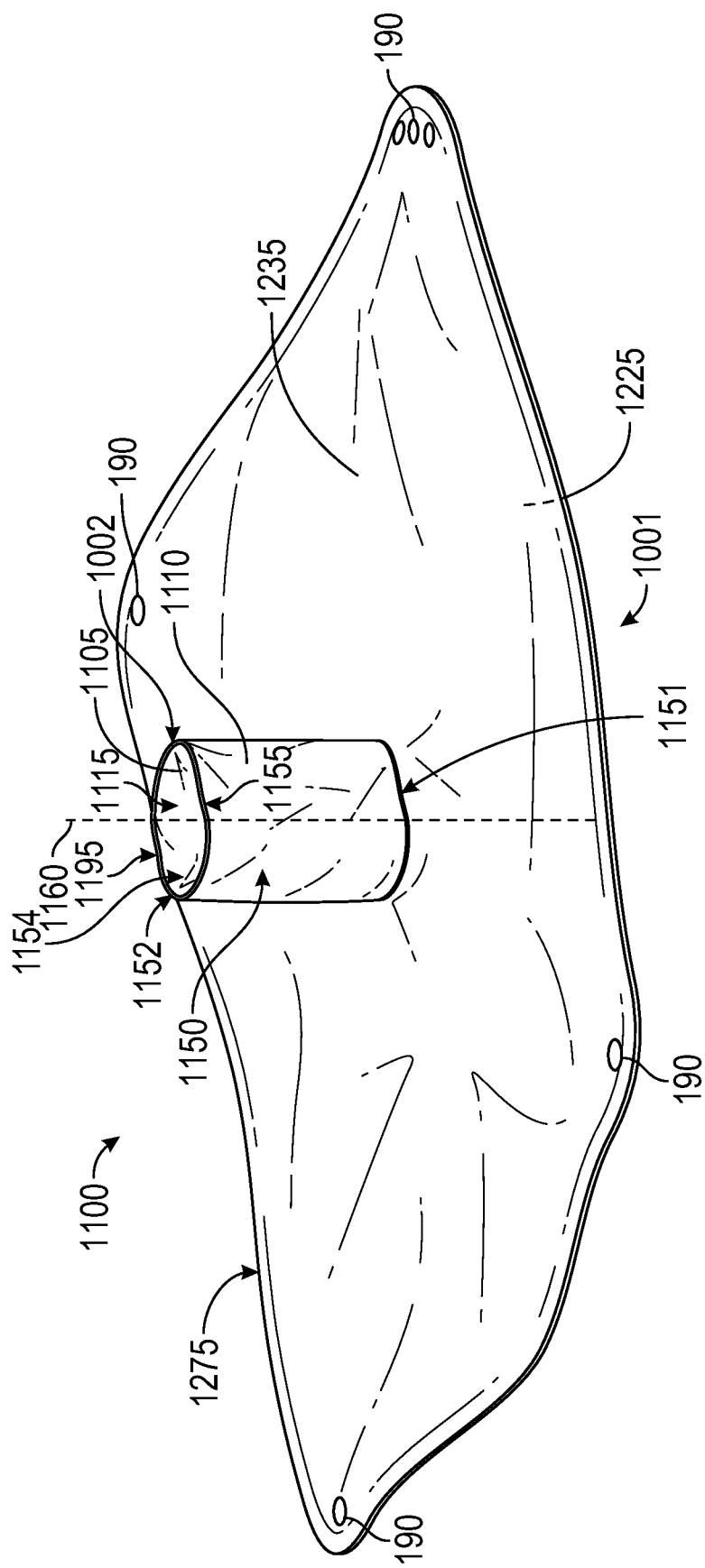
FIG. 23 is an isometric view of an implant delivery device having a substantially rectangular-shaped delivery member and a shielding member, according to an exemplary embodiment of the present disclosure.

The delivery device 1000 may include the delivery devices disclosed in U.S. Patent Publication No. 2021/0282913, also published as U.S. Pat. No. 11,116,620, the contents of each of which are incorporated by reference in their entirety for all purposes herein. Returning to FIGS. 13-17 depicting an example implant delivery device 1000, the inner bore 1115 may have a longitudinal axis 1160 extending therethrough, as shown in FIG. 23. The longitudinal axis 1160 extends substantially perpendicular to the delivery member 1275. The inner bore 1115 extends longitudinally along the longitudinal axis 1160 between the proximal end 1151 and the distal end 1152 a predetermined length 1165 (not shown in FIG. 23; see FIG. 24) away from the lower surface 1235 of the delivery member 1275. Therefore, the shielding member 1150 also extends along the longitudinal axis 1160 and substantially orthogonally from the delivery member 1275.

As depicted in FIG. 23, the delivery member 1275 extends away from shielding member 1150 in a direction substantially perpendicular to the longitudinal axis 1160. The inner bore 1115 is substantially aligned with the aperture 1220 formed in the delivery member 1275. In at least some instances, the delivery member 1275 extends away from shielding member 1150 in substantially the same plane as the aperture 1220. The aperture 1220 and inner bore 1115 of shielding member 1150 are operable to receive the implant. The proximal end 1151 of shielding member 150 is also operable to receive an implant therethrough. The distal end 1152 of shielding member 1150 is operable to be inserted into an incision in the skin of the subject and further operable to be extended the predetermined length 1165 such that the distal end 1152 is received into at least a portion of the surgically-created implant pocket or a distal portion of the dissection tunnel connecting an incision in the skin of the subject to the implant pocket. In some instances, at least a portion of the inner bore 1115 of the shielding member 1150 may extend a second predetermined length above the upper surface 1225 of the delivery member 1275 (not shown in FIGS. 23-26).

The shielding member 1150 of implant delivery device 1000 is operable to extend along at least a portion of the dissection tunnel during use. The shielding member 1150 is also operable to deliver the implant to the implant pocket or a distal portion of the dissection tunnel without the implant contacting the incision site or at least a portion of the dissection tunnel. In some instances, the shielding member 1150 of apparatus 1000 may be operable to shield the implant from touching any portion of the dissection tunnel or incision site.

While FIGS. 23-26 depict shielding member 1150 as having an inner bore 1115 that is tubular with a substantially uniform cross-sectional width 1157 along its predetermined length 165 (refer to FIG. 24), the shielding member 1150 may have an inner bore 1115 that is tubular, conical, or any combination thereof. In cases in which the inner bore 1115 of the shielding member 1150 is tubular, the inner bore 1115 of the shielding member 1150 has an uniform cross-sectional width 1157 along its predetermined length 1165. In cases in which the inner bore 1115 of the shielding member 1150 is conical, the inner bore 1115 of the shielding member 1150 has a variable cross-sectional width 1157 along its predetermined length 1165. Typically, if the shielding member 1150 has a inner bore 1115 that is conical, the inner bore 1115 has a wider cross-sectional width 1157 towards the proximal end 1151 of the shielding member 1150. For example, the cross-sectional width 1157 of the inner bore 1115 at the proximal end 1151 of the shielding member 1150 may be longer than the cross-sectional width 1157 of the inner bore 1115 at the distal end 1152 of the shielding member 1150. In such cases, the wider cross-section width 1157 at the proximal end 1151 of the shielding member 1150 may facilitate or ease insertion of the implant into the shielding member 1150.

In some instances, the shielding member 1150 may have an inner bore 1115 that is both tubular and conical. In such instances, the shielding member 1150 may comprise a tubular member and a conical member. When the shielding member 1150 has an inner bore 1115 that is both tubular and conical, the conical member generally comprises the proximal end 1151 of the shielding member 1150 while the tubular member comprises the distal end 1152 of the shielding member 1150. Accordingly, the proximal end 1151 of the inner bore 1115 of the shielding member 1150 may have a variable cross-sectional width 1157 while the distal end 1152 of the inner bore 1115 has a uniform cross-sectional width 1157.

In at least some instances, the shielding member 1150 and/or inner bore 1115 of the shielding member 1150 is substantially cylindrical in cross-sectional shape. In some instances, the shielding member 1150 and/or inner bore 1115 of the shielding member 1150 may be elliptical in cross-sectional shape. In some cases, the inner bore 1115 of shielding member 1150 is not tapered along the predetermined length 1165. In at least some instances, the distal end 1152 has substantially the same cross-sectional width as the cross-sectional width of the proximal end 1151. In such cases, the cross-sectional width 1157 of the inner bore 1115 at the distal end 1152 of the shielding member is substantially the same as the cross-sectional width 1157 of the inner bore at the proximal end 1151 of the shielding member. In some cases, the aperture 1155 of the distal end 1152 of shielding member 1150 has substantially the same cross-sectional width as the cross-sectional width of aperture 1120 in base 1175. In some cases, the cross-sectional width of the aperture 1120 in base 1175 may be substantially the same as the cross-sectional width 1157 of the proximal end 1151 of the inner bore 1115 of the tubular member 1150.

The cross-sectional width 1157 of the inner bore 1115 of the shielding member 1150 may be any cross-sectional width suitable to receive and facilitate insertion of an implant into the implant pocket of a subject. For example, the cross-sectional width 1157 of the inner bore 1115 of the shielding member 1150 may be from about 3 cm to about 12 cm, or from 3.5 cm to about 9 cm, or from about 3.5 cm to about 8.5 cm, or from about 5 cm to about 8 cm. In at least some instances, the cross-sectional width 157 of the inner bore 115 may be selected based on the size of the implant. In general, pre-filled breast implants are from about 9 cm to about 16 cm (most commonly from about 11 cm to about 12 cm) in diameter but deform and elongate when inserted into the aperture 1220 and inner bore 1115 of delivery device 1000.

As used herein, the term "cross-sectional width" shall include the longest distance between two points on the circumference or edge of the cross-section of an object having a circular and/or non-circular cross-section. The two points may be located on the interior or exterior surface circumference or edge of the cross-section of the object. It should be recognized that "cross-sectional width" of objects having a substantially circular cross-section may be referred to as the "diameter" of the object. The terms "cross-sectional width" and "diameter" may be used interchangeably for objects having a substantially circular cross-section. Understanding that the presently disclosed devices and apparatus, or portions thereof, may be deformable or collapsible or formed from collapsible or deformable materials, the cross-sectional width, as referred to herein, is generally measured in the open and/or extended configuration, such as that typical during use.

While FIGS. 23-26 depict the inner bore 1115 of the shielding member 1150 as substantially circular in cross-sectional profile, inner bore 1115 may have any cross-sectional profile, including conical, elliptical, oval, or circular. Likewise, the outer bore 1195 or outer profile of the shielding member 1150, as defined by outer surface 1110 of the shielding member 1150, may be conical, elliptical, oval, or circular. In at least some instances the distal end 1152 and the proximal end 1151 of inner bore 1115 have the same cross-sectional profile, wherein the cross-sectional profile is selected from the group consisting of circular, elliptical, and oval. For example, in cases in which the distal end 1152 and the proximal end 1151 of inner bore 1115 have the same cross-sectional profile, the cross-sectional profile of both the distal end 1152 and the proximal end 1151 of inner bore 1115 could have an elliptical cross-sectional profile, or both could have a circular cross-sectional profile, or both could have an elliptical cross-sectional profile. In other cases, the distal end 1152 of inner bore 1115 may have a cross-sectional profile that is different than the cross-sectional profile of the proximal end 1151. For example, in such cases, the distal end 1152 may have a cross-sectional profile that is elliptical while the proximal end 1151 may have a circular cross-sectional profile. In cases in which the distal end 1152 and the proximal end 1151 of inner bore have different cross-sectional profiles, they may still have the substantially the same cross-sectional width. It should be recognized that when the cross-sectional profile of a portion of the inner bore 1115 is circular, elliptical, or oval, the three-dimensional profile (e.g., the exterior profile or shape) of a corresponding portion of shielding member 1150 may also be, respectively, circular, elliptical, or oval.

The delivery member 1275 is operable to wrap around the implant to form a conforming cavity around the implant that conforms to the shape of the implant. The delivery member 1275 is also operable to propel the implant from the conforming cavity through aperture 1220 formed in the delivery member 1275 and into the inner bore 1115 of the shielding member 150 upon the application of mechanical force to the lower surface 1235 of the delivery member 1275. Therefore, delivery member 1275 is operable to deliver the implant through the shielding member 1150 and into the implant pocket of a subject thereby providing protected or no touch delivery and insertion of the implant to the implant pocket.

The shielding member 1150 is operable to deliver the implant subdermally to the implant pocket, or a distal portion of the dissection tunnel, through the predetermined length 1165 of inner bore 1115 of the shielding member 1150. In at least some instances, the predetermined length 1165 may be determined based on a distance between an incision in the skin of a patient and a surgically-created implant pocket formed below the skin. In other cases, the predetermined length 1165 may be based on a distance between an incision in the skin and the length of the dissection tunnel or portion of a dissection tunnel connecting the incision to the surgically-created implant pocket. In some instances, the predetermined length 1165 between the proximal end 1151 and the distal end 1152 extends the inner bore 1115 operably to deliver an implant subdermally through the aperture 1120 and inner bore 1115 and into the surgically-created implant pocket or a distal portion of the dissection tunnel or when the lower surface 1235 of delivery member 1275 is adjacently engaged with the skin of a subject and the distal end 1152 is received into at least a portion of the implant pocket or distal portion of the dissection tunnel.

The predetermined length 1165 of the inner bore 1115 of the shielding member 1150 may be adjusted based on the desired depth of insertion into the dissection tunnel, the size of the implant used, the location of the incision, and the characteristics of the subject's breast. In at least some instances, the predetermined length 1165 of the inner bore 1115 may have a predetermined length 1165 equal to or less than the measured length of the dissection tunnel. In some instances, the predetermined length 1165 of the inner bore 1115 of the shielding member 1150 may be greater than 1 cm, or greater than 1.5 cm, or greater than 2 cm, or greater than 2.5 cm, or greater than 3 cm, or greater than 3.5 cm, or greater than 4 cm, or greater than 4.5 cm, or greater than 5 cm, or greater than 5.5 cm, or greater than 6 cm, or greater than 6.5 cm, or greater than 7 cm, or greater than 7.5 cm, or greater than 8 cm. In other instances, the predetermined length 1165 may be from about 2 cm to about 10 cm, or from about 3 cm to about 10 cm, or from about 2 cm to about 8 cm, or from about 2 cm to about 5 cm, or from about 3 cm to about 8 cm.

The implant delivery device 1000, including shielding member 1150 and delivery member 1275, may be made of any suitable flexible material. For example, the flexible material may include, but is not limited to, plastic-containing fabrics, polymers, plastics, ethylene-vinyl acetate (EVA), polyethylene terephthalate (e.g., mylar), vinyls, polyvinyl chloride, ethylene and alpha-olefin copolymers, silicone, solid silicone, silicone rubber, and any combination thereof. In some cases, the shielding member 1150 and delivery member 1275 may be formed from the same material. In some instances, the flexible material may be resistant to stretching. In some instances, the shielding member 1150 and the delivery member 1275 may be integrally formed. In some instances, the flexible material may be a transparent or semi-transparent flexible material.

In other instances, implant delivery device 1000, including shielding member 1150 and delivery member 1275, may be stretchable and/or made of a flexible material that is stretchable. As used herein, the term "stretchable" refers to a material, or property of a device or device component, that may be extensible or elastomeric. That is, a stretchable material, or a stretchable device or device component, may be extended, deformed, or the like, without breaking, and may or may not significantly retract after removal of an extending force. As used herein, the terms "elastomeric" or "elastic" are used interchangeably to refer to that property of a material (or device or device component) where upon removal of an elongating force, the material (or device or device component) is capable of recovering to substantially an unstretched size and shape or the material exhibits a significant retractive force. As used herein, the term "extensible" refers to that property of a material (or device or device component) where upon removal of an elongating force, the material (or device or device component) experiences a substantially permanent deformation or the material does not exhibit a significant retractive force.

In particular, shielding member 1150 may be stretchable and/or comprise a stretchable material. Stretchability of the shielding member 1150 provides the advantage that when retractors are placed inside of the shielding member 1150 during use to open up the dissection tunnel, the shielding member 1150 may stretch to allow greater opening of the dissection tunnel as well as engagement of the walls of the dissection tunnel thereby providing effective shielding for the implant as well as reducing the frictional forces associated with implant insertion. The stretchability of the shielding member 1150 also provides the advantage of stretching during insertion of the implant so as to reduce the forces associated with implant insertion and to facilitate transit of the implant to the implant pocket while providing the implant shielding function, whether retractors are placed within shielding member 1150 during use or not. In at least some instances, the shielding member 1150 may be elastic or comprise an elastic material. In other instances, the shielding member 1150 may be extensible or comprise an extensible material.

In at least some instances, the shielding member 1150 may be made of a material that is different than the material that makes up the delivery member 1275. For example, while it is advantageous in at least some instances that the shielding member be stretchable or made of a stretchable material, delivery member 1275 does not necessarily need to be stretchable or made of a stretchable material. In other instances, delivery member 1275 may comprise the same material as shielding member 1150 but the stretchability of shielding member 1150 is determined by the thickness of the material. In other words, shielding member 1150 may be constructed of a material that is thin enough to be stretchable during use while the delivery member 1275 may be constructed of the same material but may not be stretchable due to the chosen thickness of the delivery member 1275.

In at least some instances, the delivery member 1275 is formed from a vinyl or polyvinyl chloride while the shielding member 1150 is formed from elastomeric silicone or silicone rubber. In other instances, both the delivery member 1275 and the shielding member 1150 may be formed from a vinyl or polyvinyl chloride or both the delivery member 1275 and the shielding member 1150 may be formed from elastomeric silicone or silicone rubber. In at least some instances, the delivery member 1275 may be formed from a material that is fairly elastic to mildly elastic while the shielding member 1150 may be formed from a material that is slightly stretchable to elastic. In at least some instances, the joint or intersection between the delivery member and the shielding member is heat sealed or sealed with a glue or adhesive.

In some cases, the inner bore 1115 may include a lubricant along the inner surface 105 that defines the inner bore 1115. In such cases, the lubricant along the inner surface 1105 of the inner bore 1115 may facilitate insertion and passage of the implant into and through aperture 1120 and inner bore 1115. In some instances, the outer surface 1110 of the shielding member 1150 may include a lubricant. In such cases, the lubricant on the outer surface 1110 may facilitate insertion of the shielding member 1150 into the dissection tunnel. The lubricant may be, for example, a sterile lubricant selected from the group consisting of a surgical lubricant, a water-based lubricating jelly, a dry lubricant, a powdered lubricant, a moisture-activated lubricant, and any combination thereof. The lubricant may be disposed on the inner surface 1105 and/or the outer surface 1110 at the time of manufacturing and packing. In other instances, the lubricant may be applied to the inner surface 1105 and/or the outer surface 1110 by a physician or technician prior to use so long as the surfaces and the lubricant remain sterile.

In some instances, the inner bore 1115 or inner surface 1105 of shielding member 1150 may include a lubricating coating or a friction-reducing coating that serves a similar function as the lubricant described above. In some cases, the outer surface 1110 of the shielding member 1150 may include a lubricating coating or a friction-reducing coating that also serves the same or similar function as the lubricant described above.

Figure 22:
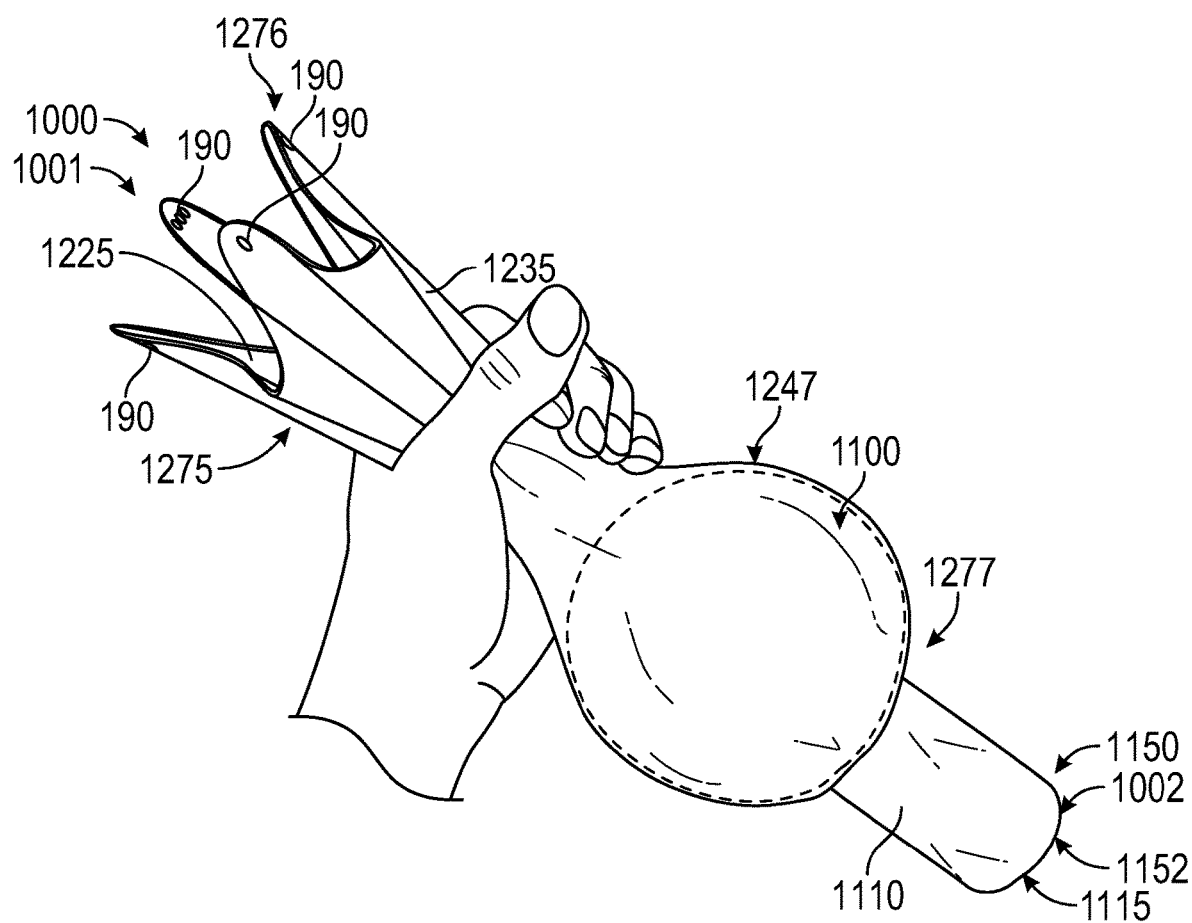
FIG. 22 is a diagrammatic view of the implant delivery device having an implant wrapped therein, according to an exemplary embodiment of the present disclosure.
Figure 24:
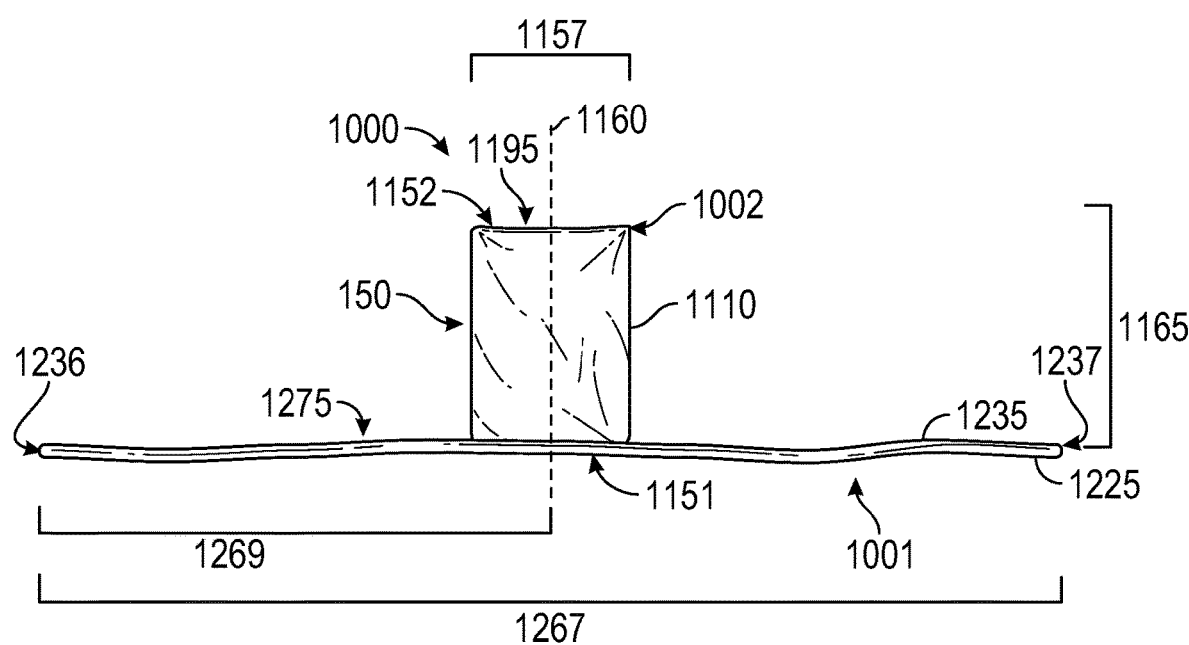
FIG. 24 is a planar view of an implant delivery device having a substantially rectangular-shaped delivery member, according to an exemplary embodiment of the present disclosure.

FIG. 24 is a planar view of the implant delivery device 1000, according to an exemplary embodiment of the present disclosure. As depicted in FIG. 24, implant delivery device 1000 includes delivery member 1275 and shielding member 1150 extending through the delivery member 1275 to form aperture 1220 (not shown in FIG. 24; see FIG. 26). The shielding member 1150 has an inner bore 1115, a proximal end 1151 and a distal end 1152. The delivery member 1275 radially extends from at least a portion of the proximal end 1151 of shielding member 1150. The inner bore 1115 has a longitudinal axis 1160 therethrough which extends substantially perpendicular and/or orthogonally to the delivery member 1275. As shown in FIG. 22, the inner bore 1115 extends longitudinally a predetermined length 1165 away from the lower surface 1235 of the delivery member 1275 and between the proximal end 1151 and the distal end 1152. The shielding member 150 likewise extends along the longitudinal axis 160 a predetermined length 1165 away from the lower surface 1235 of the delivery member 1275 and substantially perpendicular and/or orthogonally to the delivery member 1275.

Figure 25:
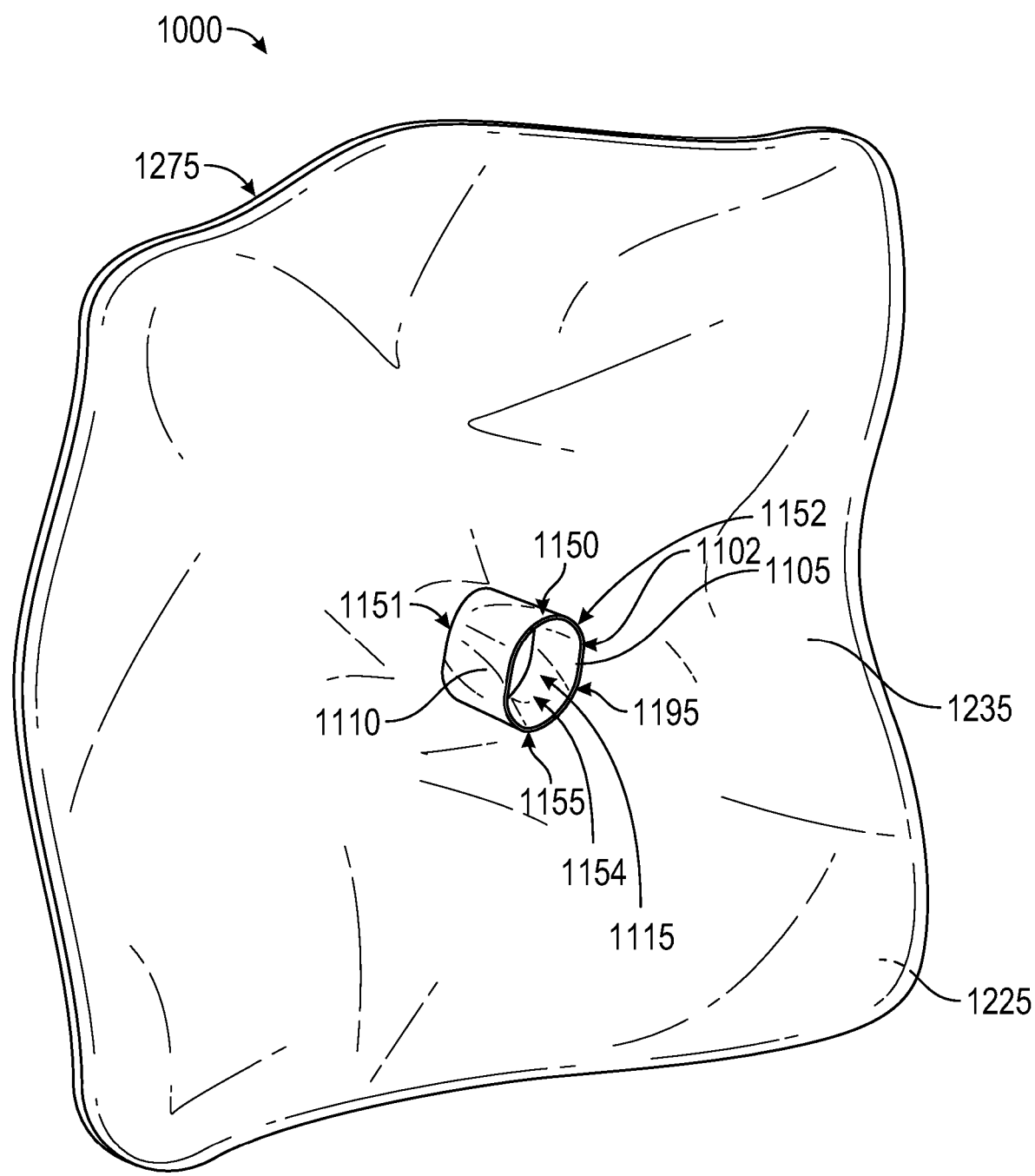
FIG. 25 is a front diagrammatic view of an implant delivery device showing the distal end of the shielding member and the lower surface of the substantially rectangular-shaped delivery member, according to an exemplary embodiment of the present disclosure.
Figure 26:
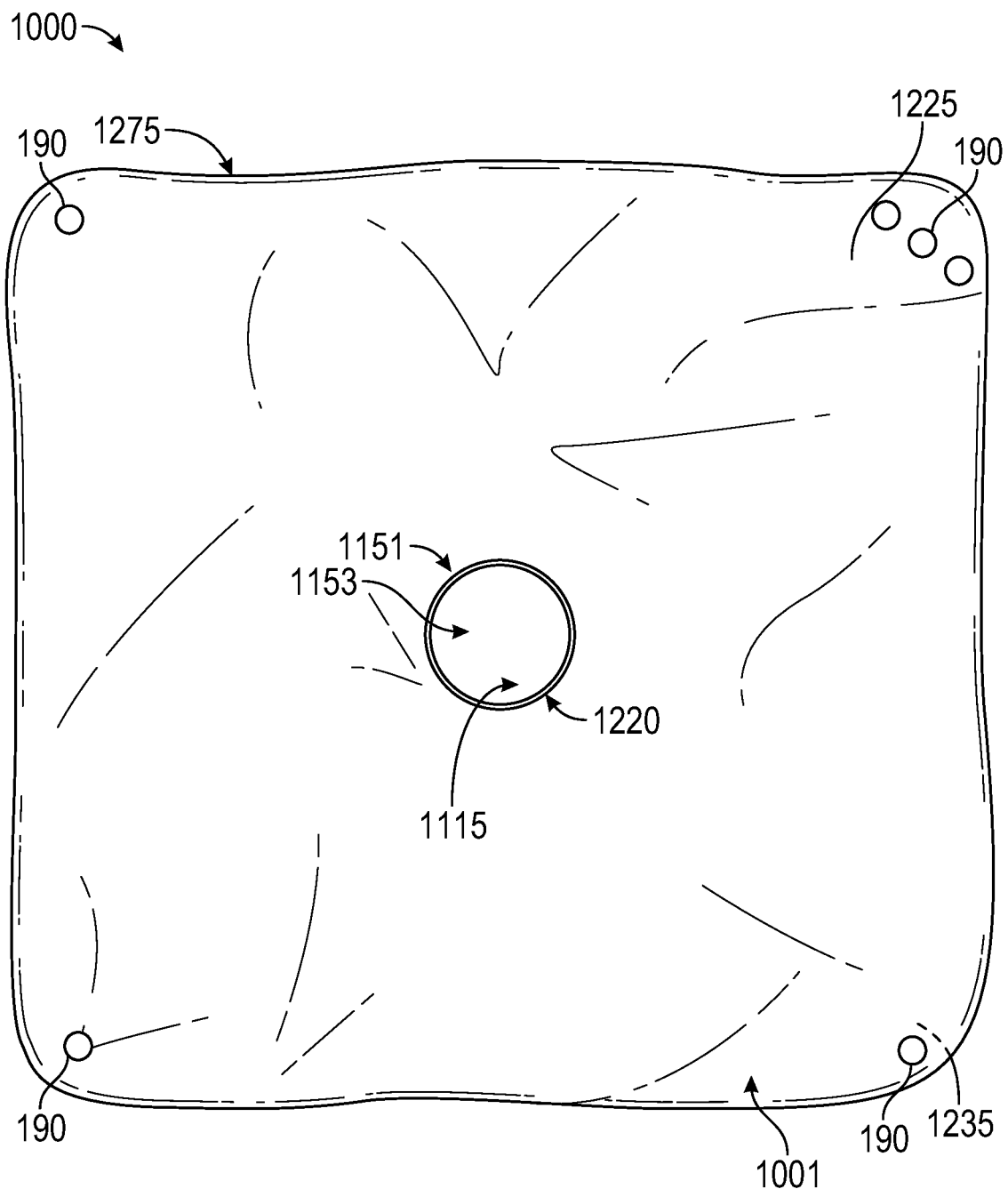
FIG. 26 is a rear planar view of the implant delivery device showing the aperture formed in the delivery member coupled with the proximal end of the shielding member and the upper surface of the substantially rectangular-shaped delivery member, according to an exemplary embodiment of the present disclosure.

FIG. 25 is a front diagrammatic view of the implant delivery device 1000 showing the distal end 1152 of shielding member 1150 and the lower surface 1235 of the delivery member 1275, according to an exemplary embodiment of the present disclosure. As depicted in FIG. 25, the proximal end 1151 of shielding member 1150 is coupled with delivery member 1275 of the implant delivery device 1000. The distal end 1152 of the shielding member 1150 comprises aperture 1155 through which an implant may exit after transiting through at least a portion of the dissection tunnel during delivery to the implant pocket. FIG. 26 is a rear diagrammatic view of the implant delivery device 100 showing delivery member 1275 having an aperture 1220 formed therein and extending through the upper surface 1225 and the lower surface 1235 of the delivery member 1275.

The delivery member 1275 can have any shape, configuration, diameter, or thickness so long as the delivery member 1275 is operable to wrap around the implant to form a conforming cavity around the implant that conforms to the shape of the implant and so long as the delivery member 1275 is operable to cause the translation of the implant from the conforming cavity through aperture 1220 and the inner bore 1115 of the shielding member 1150 upon the application of mechanical force to the lower surface 1235 of the delivery member 1275. For example, in at least some instances, the delivery member 1275 may be substantially rectangular as shown in FIGS. 23-26, or the delivery member 1275 may be, for example, substantially circular.

As depicted in FIG. 24, the delivery member 1275 may have a diameter 1267. As used herein, the diameter 1267 of the delivery member 1275 is defined as the minimum distance between two opposite outer edges of the delivery member 1275 when the delivery member 1275 is fully extended away from the shielding member 1150 (e.g., the same position or configuration as when the delivery member is lying flat and extended on a flat surface). For example, as shown in FIG. 22, the diameter 1267 of delivery member 1275 is the distance between first outer edge 1236 and an opposite second outer edge 1237. The delivery member 1275 may have any diameter 1267 sufficient to be operable to wrap around the implant to form a conforming cavity around the implant that conforms to the shape of the implant. The delivery member 1275 may also have any diameter 1267 sufficient to be operable to cause the translation of the implant from the conforming cavity through aperture 1220 and the inner bore 1115 of the shielding member 1150 upon the application of mechanical force to the lower surface 1235 of the delivery member 1275.

In at least some instances, the delivery member 1275 may have a diameter 1267 that is at least 3 times greater than the cross-sectional width 1157 of the inner bore 1115 of the shielding member 1150 and/or the aperture 1220 and/or the outer bore 1195 of the shielding member 1150. In other instances, the delivery member 1275 may have a diameter 1267 that is at least 4 times greater than the cross-sectional width 1157 of the inner bore 1115 of the shielding member 1150 and/or the aperture 1220 and/or the outer bore 1195 of the shielding member 1150. In still other cases, the delivery member 1275 may have a diameter 1267 that is at least 5 times greater than the cross-sectional width 1157 of the inner bore 1115 of the shielding member 1150 and/or the aperture 1220 and/or the outer bore 1195 of the shielding member 1150. In other instances, the delivery member 1275 may have a diameter 1267 that is at least 6 times greater than the cross-sectional width 1157 of the inner bore 1115 of the shielding member 1150 and/or the aperture 1220 and/or the outer bore 1195 of the shielding member 1150. In other cases, the delivery member 1275 may have a diameter 1267 that is at least 7 times greater than the cross-sectional width 1157 of the inner bore 1115 of the shielding member 1150 and/or the aperture 1220 and/or the outer bore 1195 of the shielding member 1150. In still other cases, the delivery member 1275 may have a diameter 1267 that is at least 8 times greater than the cross-sectional width 1157 of the inner bore 1115 of the shielding member 1150 and/or the aperture 1220 and/or the outer bore 1195 of the shielding member 1150. In still even other instances, the delivery member 1275 may have a diameter 1267 that is at least 10 times greater than the cross-sectional width 1157 of the inner bore 1115 of the shielding member 1150 and/or the aperture 1220 and/or the outer bore 1195 of the shielding member 1150.

In at least some instances, the delivery member 1275 may have a diameter 1267 that is more than 3 times greater than the cross-sectional width 1157 of the inner bore 1115 of the shielding member 1150 and/or the aperture 1220 and/or the outer bore 1195 of the shielding member 1150. In other instances, the delivery member 1275 may have a diameter 1267 that is more than 4 times greater than the cross-sectional width 1157 of the inner bore 1115 of the shielding member 1150 and/or the aperture 1220 and/or the outer bore 1195 of the shielding member 1150. In still other cases, the delivery member 1275 may have a diameter 1267 that is more than 5 times greater than the cross-sectional width 1157 of the inner bore 1115 of the shielding member 1150 and/or the aperture 1220 and/or the outer bore 1195 of the shielding member 1150. In other instances, the delivery member 1275 may have a diameter 1267 that is more than 6 times greater than the cross-sectional width 1157 of the inner bore 1115 of the shielding member 1150 and/or the aperture 1220 and/or the outer bore 1195 of the shielding member 1150. In other cases, the delivery member 1275 may have a diameter 1267 that is more than 7 times greater than the cross-sectional width 1157 of the inner bore 1115 of the shielding member 1150 and/or the aperture 1220 and/or the outer bore 1195 of the shielding member 1150. In still other cases, the delivery member 1275 may have a diameter 1267 that is more than 8 times greater than the cross-sectional width 1157 of the inner bore 1115 of the shielding member 1150 and/or the aperture 1220 and/or the outer bore 1195 of the shielding member 1150. In still even other instances, the delivery member 1275 may have a diameter 1267 that is more than 10 times greater than the cross-sectional width 1157 of the inner bore 1115 of the shielding member 1150 and/or the aperture 1220 and/or the outer bore 1195 of the shielding member 1150.

In at least some aspects, the delivery member 1275 may have a diameter 1267 that is from about 5 times to about 8 times greater than the cross-sectional width 1157 of the inner bore 1115 of the shielding member 1150 and/or the aperture 1220 and/or the outer bore 1195 of the shielding member 1150. In other aspects, the delivery member 1275 may have a diameter 1267 that is from about 6 times to about 8 times greater than the cross-sectional width 1157 of the inner bore 1115 of the shielding member 1150 and/or the aperture 1220 and/or the outer bore 1195 of the shielding member 1150. In still other aspects, the delivery member 1275 may have a diameter 1267 that is from about 4 times to about 8 times greater than the cross-sectional width 1157 of the inner bore 1115 of the shielding member 1150 and/or the aperture 1220 and/or the outer bore 1195 of the shielding member 1150. In yet further aspects, the delivery member 1275 may have a diameter 1267 that is from about 5 times to about 10 times greater than the cross-sectional width 1157 of the inner bore 1115 of the shielding member 1150 and/or the aperture 1220 and/or the outer bore 1195 of the shielding member 1150.

In at least some aspects, the cross-sectional width of the inner bore may be from about 3.5 cm to about 8 cm. In other aspects, the cross-sectional width of the inner bore is from about 2 cm to about 10 cm. In some instances, the diameter of the delivery member 1275 is from about 17.5 cm to about 40 cm, or from about 10 cm to about 50 cm, or from about 21 cm to about 48 cm, or from about 12 cm to about 60 cm, or from about 24.5 cm to about 56 cm, or from about 14 cm to about 70 cm, or from about 28 cm to about 64 cm, or from about 16 cm to about 80 cm, or from about 35 cm to about 80 cm, or from about 20 cm to about 100 cm.

Figure 13:
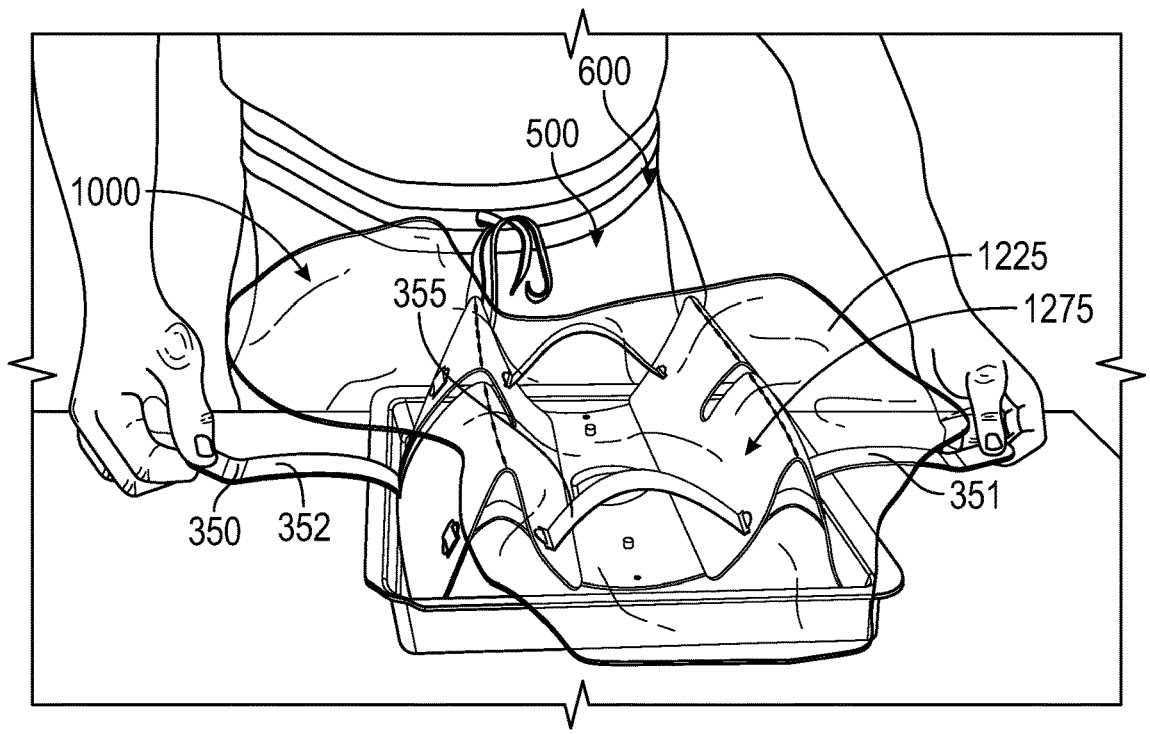
FIG. 13 is an isometric perspective view of a loading apparatus having a pop-up portion in an extended deployed second configuration with the distal end of a delivery received in the receiving portion and a proximal end of the delivery device received on two opposing inclined guide portions, according to an exemplary embodiment of the present disclosure.

The delivery member 1275 may also have a radial length 1269, as shown in FIG. 13. As used herein, the radial length 1269 of delivery member 1275 is defined as the distance between an outer edge (e.g., outer edges 1236, 1237) of the delivery member 1275, when the delivery member 1275 is fully extended away from the shielding member 1150 (e.g., the same position or configuration as when the base is lying flat on a flat surface and extending away from the shielding member 1150), and the outer surface 1110 of the proximal end 1151 of the shielding member 1150 where it is coupled to the delivery member 1275. Accordingly, the radial length 1269 of the delivery member is the length that the delivery member 1275 extends away from the shielding member 1150. The delivery member 1275 may have any radial length sufficient to be operable to wrap around the implant to form a conforming cavity around the implant that conforms to the shape of the implant. The delivery member 1275 may also have any radial length 1269 sufficient to be operable to cause the translation of the implant from the conforming cavity through aperture 1220 and the inner bore 1115 of the shielding member 1150 upon the application of mechanical force to the lower surface 1235 of the delivery member 1275.

Delivery member 1275 may have sufficient thickness to provide structural support or rigidity to be operable to propel the implant from the conforming cavity through aperture 1220 formed in the delivery member 1275 and into the inner bore 1115 of the shielding member 1150 upon the application of mechanical force to the lower surface 1235 of the delivery member 1275. In some instances, the delivery member 1275 may have a thickness (e.g., the distance or thickness between the lower surface 1235 and the upper surface 1225 of delivery member 1275) that is substantially the same as the thickness of the shielding member 1150. In other instances, the delivery member 1275 may have a thickness that is substantially thicker than the thickness of the shielding member 1150. In other instances, the delivery member 1275 may have a thickness that is substantially thinner than the thickness of the shielding member 1150. In such instances, the shielding member 1150 may be thicker than the thickness of the delivery member 1275 so that the shielding member 1150 has sufficient rigidity or structural integrity to facilitate insertion into the dissection tunnel while resisting the forces created by insertion of the implant into the inner bore 1115 such that the shielding member 1150 is operable to shield the implant from the dissection tunnel during transit of the implant along the inner bore to the implant pocket.

Statements of the Disclosure:

Statement 1: A loading apparatus for facilitating the loading of an implant into an implant delivery device, the apparatus comprising: a receiving portion operable to receive at least a portion of the implant delivery device such that movement of the implant delivery device is mitigated during loading of an implant into the delivery device or onto a surface of the delivery device.

Statement 2: The loading apparatus according to Statement 1, wherein the receiving portion is configured to receive a distal end of the implant delivery device.

Statement 3: The loading apparatus according to Statement 1 or Statement 2, wherein the receiving portion comprises a shape that is complementary to the shape of the distal end of the implant delivery device so that the receiving portion is configured to receive a distal end of the implant delivery device.

Statement 4: The loading apparatus according to any one of Statements 1-3, wherein the receiving portion is operable to positionally fix or stabilize the implant delivery device during loading when the implant delivery device or a portion thereof is received in the receiving portion.

Statement 5: The loading apparatus according to any one of Statements 1-3, wherein the receiving portion is operable to resist movement of the implant delivery device during loading when the implant delivery device or a portion thereof is received in the receiving portion.

Statement 6: The loading apparatus according to any one of Statements 1-3, wherein the receiving portion is operable to arrest movement of the implant delivery device during loading when the implant delivery device or a portion thereof is received in the receiving portion.

Statement 7: The loading apparatus according to any one of Statements 1-6, further comprising: a tray portion having an upper surface, a lower surface, an outer edge extending around the upper and lower surfaces, and a wall extending around the outer edge such that the wall, together with the upper surface, forms a reservoir.

Statement 8: The loading apparatus according to Statement 7, wherein the receiving portion extends from the upper surface of the tray portion.

Statement 9: The loading apparatus according to Statement 8, wherein the receiving portion comprises at least one selected from the group consisting of a retaining ring, a friction fit component, a clip, and a sleeve.

Statement 10: The loading apparatus according to Statement 9, wherein the receiving portion comprises a retaining ring that is under tension such that when the implant delivery device or a portion thereof is received in the receiving portion, the tension is operable to resist movement of the implant delivery device during loading.

Statement 11: The loading apparatus according to Statement 10, wherein the tension is produced by one or more springs.

Statement 12: The loading apparatus according to Statement 11, wherein the receiving portion comprises a spring-loaded retaining ring.

Statement 13: The loading apparatus according to any one of Statements 7-12, wherein the receiving portion is located substantially near the center of the upper surface of the tray portion.

Statement 14: The loading apparatus according to any one of Statements 1-13, wherein the receiving portion comprises one or more walls.

Statement 15: The loading apparatus according to Statement 14, wherein the one or more walls forms a cavity or channel operable to receive the distal end of the implant delivery device, or a portion thereof.

Statement 16: The loading apparatus according to Statement 14, wherein the one or more walls forms a recessed receiving portion operable to receive the distal end of the implant delivery device, or a portion thereof, therein.

Statement 17: The loading apparatus according to any one of Statements 14-16, wherein the receiving portion comprises at least two opposing walls the two opposing walls being substantially perpendicular to the upper surface of the tray portion.

Statement 18: The loading apparatus according to any one of Statements 14-17, wherein the receiving portion comprises a channel or cavity comprising one or more walls defining the channel or cavity.

Statement 19: The loading apparatus according to any one of Statements 14-17, wherein the receiving portion comprises a channel or cavity comprising at least two opposing walls defining the channel or cavity.

Statement 20: The loading apparatus according to any one of Statements 1-19, further comprising: a pop-up portion operable to deploy from a substantially flat undeployed first configuration to an extended deployed second configuration, the extended second configuration comprising at least one inclined guide portion.

Statement 21: The loading apparatus according to Statement 20, wherein the pop-up portion comprises the receiving portion.

Statement 22: The loading apparatus according to Statement 21, wherein the receiving portion is a recessed receiving portion located substantially near the center of the pop-up portion.

Statement 23: The loading apparatus according to Statement 20, wherein the pop-up portion comprises an aperture substantially near the center of the pop-up portion, wherein the aperture is operable to receive the receiving portion on the tray portion.

Statement 24: The loading apparatus according to Statement 23, wherein the receiving portion of the tray portion is coupled to the pop-up portion at the aperture.

Statement 25: The loading apparatus according to any one of Statements 20-24, wherein the pop-up portion is operable to be retained within the reservoir of the tray portion.

Statement 26: The loading apparatus according to any one of Statements 20-25, wherein the reservoir is operable to completely contain the pop-up portion when the pop-up portion is in the substantially flat undeployed first configuration.

Statement 27: The loading apparatus according to any one of Statements 20-26, wherein the pop-up portion comprises an extendable member and an elevatable member, the extendable member coupled to the elevatable member such that when the extendable member is extended the elevatable member is elevated to form at least one inclined guide portion.

Statement 28: The loading apparatus according to Statement 27, wherein the extendable member is folded beneath the elevatable member when the pop-up portion is in the undeployed first configuration.

Statement 29: The loading apparatus according to Statement 27 or Statement 28, wherein the pop-up portion comprises one or more push or pull tabs coupled to the extendable member, the extendable member configured to extend upon application of force to the push or pull tab.

Statement 30: The loading apparatus according to Statement 29, wherein the pop-up portion is operable to deploy from the undeployed first configuration to the deployed extended second configuration upon the application of force to the push or pull tab.

Statement 31: The loading apparatus according to any one of Statements 27-30, wherein the tray portion is configured such that the travel of the extendable member during extension is limited by contact with an opposing wall of the tray portion.

Statement 32: The loading apparatus according to any one of Statements 20-31, wherein the pop-up portion comprises: a first extendable member coupled to a first elevatable member; and a second extendable member coupled to a second elevatable member; the pop-up portion operable such that when the first and second extendable members are extended, the first and second elevatable members are elevated to each form an inclined guide portion and a opposing inclined guide portion, respectively, such that the inclined guide portion and the opposing inclined guide portions substantially form a U-shape or a V-shape with respect to the upper surface of the tray portion.

Statement 33: The loading apparatus according to Statement 32, wherein the first extendable member is coupled to a first push or pull tab and the second extendable member is coupled to a second push or pull tab, the first and second extendable members configured to extend upon application of force to a respective one of the first and second push or pull tabs.

Statement 34: The loading apparatus according to Statement 33, wherein the pop-up portion is operable to deploy from the undeployed first configuration to the deployed extended second configuration upon the application of force to the first and second push or pull tabs.

Statement 35: The loading apparatus according to any one of Statements 32-34, wherein the pop-up portion further comprises one or more travel limiters, the one or more travel limiters coupling the first elevatable member to the second elevatable thereby limiting travel or inclination of the first and second elevatable members during extension of the first and second extendable members.

Statement 36: The loading apparatus according to any one of Statements 20-35, further comprising one or more retaining mechanisms operable to couple the pop-up portion to the tray portion so that at least a portion of the pop-up portion is anchored to the tray portion.

Statement 37: The loading apparatus according to any one of Statements 20-35, further comprising one or more retaining mechanisms operable to couple the pop-up portion to the tray portion so that at least a portion of the pop-up portion is retained in the reservoir of the tray portion during deployment of the pop-up portion from the first configuration to the second configuration.

Statement 38: The loading apparatus according to Statement 36 or Statement 37, wherein the retaining mechanism is a retaining pin or a retaining clip.

Statement 39: The loading apparatus according to any one of Statements 29-38, wherein the one or more push or pull tabs are integrally formed from one or more extendable members.

Statement 40: The loading apparatus according to any one of Statements 29-39, wherein the one or more push or pull tabs are formed from the same material that constitutes the one or more extendable members.

Statement 41: The loading apparatus according to any one of Statements 7-40, wherein the wall of tray portion is substantially vertical or perpendicular to the upper surface of the tray portion.

Statement 42: The loading apparatus according to any one of Statements 7-40, wherein the wall of tray portion is substantially inclined or obtuse to the upper surface of the tray portion.

Statement 43: The loading apparatus according to any one of Statements 7-42, wherein the tray portion further comprises a lip coupled with an upper edge of the wall, the lip being substantially perpendicular to the wall.

Statement 44: The loading apparatus according to any one of Statements 7-42, wherein the tray portion further comprises a lip coupled with an upper edge of the wall, the lip being substantially parallel to the upper surface of the tray portion.

Statement 45: The loading apparatus according to any one of Statements 1-44, further comprising a lid portion, the lid portion comprising a top surface, a bottom surface, and an edge, the lid portion operable to engage a portion of the tray portion in order to substantially enclose the reservoir of the tray portion.

Statement 46: The loading apparatus according to Statement 45, wherein the lip of tray portion is operable to engage with a bottom surface or an edge of the lid portion thereby substantially enclosing the reservoir of the tray portion.

Statement 47: The loading apparatus according to Statement 45 or Statement 46, wherein the lid portion is configured to engage with a portion of the tray portion so as to substantially enclose the pop-up portion in the reservoir of the tray portion.

Statement 48: The loading apparatus according to any one of Statements 45-47, wherein the lid portion is operable to engage with a portion of the tray portion so as to sterilely seal the reservoir such that the implant delivery device at least partially received in the receiving portion is maintained in a sterile condition prior to use.

Statement 49: The loading apparatus according to any one of Statements 20-48, wherein the pop-up portion is operable to deploy from a substantially flat undeployed first configuration to an elevated and deployed second configuration, the elevated and deployed second configuration comprising one or more inclined surfaces in the form of one or more inclined guide portions operable to receive at least a portion of the implant delivery device.

Statement 50: The loading apparatus according to any one of Statements 20-49, wherein the at least one inclined guide portion is operable to receive a portion of the delivery device when the delivery device, or a portion thereof, is received in the receiving portion.

Statement 51: The loading apparatus according to any one of Statements 20-50, wherein when the delivery device or a at least a portion thereof is received in the recessed receiving portion, the at least one inclined guide portion is operable to receive the implant and guide it toward the recessed receiving portion such that at least a portion of the implant is received in the implant delivery device, or portion thereof, received in the recessed receiving portion.

Statement 52: The loading apparatus according to any one of Statements 1-51, wherein the recessed receiving portion is operable to receive the implant such that a leading edge of the implant is at least partially received in the receiving portion.

Statement 53: The loading apparatus according to any one of Statements 1-52, wherein the recessed receiving portion is operable to receive the implant, or a portion thereof, such that the implant is oriented properly in the implant delivery device.

Statement 54: The loading apparatus according to any one of Statements 7-53, wherein the reservoir is operable to receive and retain a liquid wetting solution for wetting the delivery device.

Statement 55: The loading apparatus according to Statement 54, wherein the at least one inclined guide portion is operable to direct a liquid wetting solution to the receiving portion.

Statement 56: The loading apparatus according to Statement 54 or Statement 55, wherein the at least one inclined guide portion is in fluid communication with the receiving portion.

Statement 57: The loading apparatus according to any one of Statements 20-56, wherein the at least one inclined guide portion comprises at least one selected from the group consisting of an inclined ramp, a conical surface, a curvilinear surface, a curved surface, a trapezoidal surface, and any combination thereof.

Statement 58: The loading apparatus according to any one of Statements 1-57, wherein the receiving portion comprises a channel selected from the group consisting of a rectangular channel, a circular channel, a conical channel, a polygonal channel, an oval channel, and any combination thereof.

Statement 59: The loading apparatus according to any one of Statements 20-58, wherein the at least one inclined guide portion comprises a first length and a second length, wherein the first length comprises from about 2 cm to about 15 cm and the second length comprises from about 8 cm to about 20 cm.

Statement 60: The loading apparatus according to any one of Statements 1-59, wherein the receiving portion comprises a channel having a cross-sectional width that is greater than the projection of the implant.

Statement 61: The loading apparatus according to Statement 60, wherein the channel has a cross-sectional width from about 2 cm to about 7 cm.

Statement 62: The loading apparatus according to Statement 60 or Statement 61, wherein the channel has a depth of from about 1 cm to about 10 cm.

Statement 63: The loading apparatus according to any one of Statements 7-62, wherein the tray portion is a rectangular tray or a circular tray.

Statement 64: The loading apparatus according to any one of Statements 1-63, wherein the implant delivery device comprises a proximal end operable for receiving the implant during loading and a distal end operable to be contacted with an incision in the subject during delivery of the implant into an implant pocket in the subject; wherein the receiving portion is operable to receive at least a portion of the distal end of the implant delivery device.

Statement 65: The loading apparatus according to any one of Statements 1-64, wherein the implant delivery device comprises: a delivery member having an upper surface and a lower surface, the delivery member having an aperture formed therein and extending through the upper surface and the lower surface; and a shielding member coupled with the delivery member, the shielding member having an inner bore extending longitudinally between a proximal end having a proximal opening and a distal end having a distal opening, the inner bore extending a predetermined length away from the lower surface of the delivery member; wherein the proximal end of the shielding member is coupled with the delivery member and the inner bore is substantially aligned with the aperture formed in the delivery member; wherein the delivery member is operable to wrap around the implant to form a conforming cavity around the implant that conforms to the shape of the implant; and wherein the inner bore is operable to receive the implant therethrough when mechanical force is applied to the lower surface of the delivery member; wherein the receiving portion is operable to receive at least a portion of the shielding member of the implant delivery device.

Statement 66: The loading apparatus according to any one of Statements 1-66, wherein the implant delivery device is operable to deliver an implant into a surgically-created implant pocket in a subject.

Statement 67: The loading apparatus according to any one of Statements 1-66, wherein the loading apparatus is for orienting an implant in an implant delivery device during loading of the implant into the implant delivery device.

Statement 68: The loading apparatus according to any one of Statements 1-67, wherein the loading apparatus is for fixing or anchoring an implant delivery device during loading of the implant into the implant delivery device.

Statement 69: The loading apparatus according to any one of Statements 64-68, wherein the proximal end of the delivery device comprises a plurality of fasteners, the plurality of fasteners spaced apart along the proximal end of the delivery device such that one or more opposing fasteners may be fastened so as to prevent gross movement of the implant during handling of the loaded implant delivery device prior to insertion of the implant into the implant pocket of the subject.

Statement 70: The loading apparatus according to Statement 69, wherein the plurality of fasteners is selected from the group consisting of a snap, a button, a clip, a tab, and any combination thereof.

Statement 71: A system for facilitating the loading of an implant into an implant delivery device, the system comprising: a loading apparatus according to any one of Statements 1-70; and an implant delivery device operable to deliver an implant into a surgically-created implant pocket in a subject.

Statement 72: The system according to Statement 71, wherein the implant delivery device comprises a proximal end operable for receiving the implant during loading and a distal end operable to be contacted with an incision in the subject during delivery of the implant into an implant pocket in the subject; wherein the receiving portion is operable to receive at least a portion of the distal end of the implant delivery device.

Statement 73: The system according to Statement 71 or Statement 72, wherein the implant delivery device comprises: a delivery member having an upper surface and a lower surface, the delivery member having an aperture formed therein and extending through the upper surface and the lower surface; and a shielding member coupled with the delivery member, the shielding member having an inner bore extending longitudinally between a proximal end having a proximal opening and a distal end having a distal opening, the inner bore extending a predetermined length away from the lower surface of the delivery member; wherein the proximal end of the shielding member is coupled with the delivery member and the inner bore is substantially aligned with the aperture formed in the delivery member; wherein the delivery member is operable to wrap around the implant to form a conforming cavity around the implant that conforms to the shape of the implant; and wherein the inner bore is operable to receive the implant therethrough when mechanical force is applied to the lower surface of the delivery member; wherein the receiving portion is operable to receive at least a portion of the shielding member of the implant delivery device.

Statement 74: The system according to any one of Statements 71-73, wherein the loading apparatus is for orienting an implant in an implant delivery device during loading of the implant into the implant delivery device.

Statement 75: The system according to any one of Statements 71-74, wherein the loading apparatus is for fixing or anchoring the implant delivery device during loading of the implant into the implant delivery device.

Statement 76: The system according to any one of Statements 71-75, wherein the proximal end of the delivery device comprises a plurality of fasteners, the plurality of fasteners spaced apart along the proximal end of the delivery device such that one or more opposing fasteners may be fastened so as to prevent gross movement of the implant during handling of the loaded implant delivery device prior to insertion of the implant into the implant pocket of the subject.

Statement 77: The system according to Statement 76, wherein the plurality of fasteners is selected from the group consisting of a snap, a button, a clip, a tab, and any combination thereof.

Statement 78: The system according to any one of Statements 71-77, further comprising: an implant.

Statement 79: A method of loading an implant into an implant delivery device, the method comprising: providing a loading apparatus having a receiving portion operable to receive at least a portion of the implant delivery device, the loading device having at least one inclined guide portion; providing an implant delivery device having a proximal end operable for receiving the implant during loading and a distal end operable to be contacted with an incision in the subject during delivery of the implant into an implant pocket in the subject, wherein at least a portion of the proximal end of the implant delivery device is disposed about the at least one inclined guide portion and at least a portion of the distal end of the implant delivery device is received in the receiving portion; depositing an implant onto the proximal end, or portion thereof, of the implant delivery device disposed about the at least one inclined guide portion such that the implant is caused to translate down the inclined guide portion towards the receiving portion such that at least a portion of the leading edge of the implant is received into the distal end of the implant delivery device received in the receiving portion.

Statement 80: The method according to Statement 79, wherein the loading apparatus is a loading apparatus according to any one of Statements 1-63.

Statement 81: The method according to Statement 79 or Statement 80, wherein the loading apparatus further comprises: a pop-up portion operable to deploy from a substantially flat undeployed first configuration to an extended deployed second configuration, the extended second configuration comprising at least one inclined guide portion.

Statement 82: The method according to Statement 81, further comprising: causing the pop-up portion to deploy from a substantially flat undeployed first configuration to an extended deployed second configuration having at least one inclined guide portion.

Statement 83: The method according to Statement 82, wherein the substantially flat undeployed first configuration does not have at least one inclined guide portion.

Statement 84: The method according to Statement 82 or Statement 83, wherein causing the pop-up portion to deploy comprises the application of force to one or more push or pull tabs.

Statement 85: The method according to any one of Statements 82-84, further comprising: causing the pop-up portion to deploy from a substantially flat undeployed first configuration to an extended deployed second configuration having a plurality of inclined guide portions, the plurality of inclined guide portions arranged in opposition to substantially form a U-shape or a V-shape configured to receive at least a portion of the proximal end of the implant delivery device.

Statement 86: The method according to any one of Statements 79-85, further comprising: removing a lid portion enclosing the delivery device disposed in a reservoir of the loading apparatus.

Statement 87: The method according to any one of Statements 79-86, further comprising: unfolding one or more portions of the proximal end of the delivery device in order to prepare the delivery device for receiving the implant.

Statement 88: The method according to any one of Statements 79-87, further comprising: causing the implant delivery device to be placed on the loading device such that at least a portion of the distal end of the implant delivery device is received in the receiving portion and at least a portion of the proximal end of the implant delivery device is disposed about the at least one inclined guide portion.

Statement 89: The method according to any one of Statements 80-88, further comprising: causing the proximal end of the implant delivery device to wrap around the implant to generate an implant delivery device with the implant loaded with the leading edge of the implant oriented toward the distal end of the implant delivery device.

Statement 90: The method according to any one of Statements 79-89, wherein depositing an implant onto the proximal end, or portion thereof, of the implant delivery device disposed about the at least one inclined guide portion comprises: pouring the implant from a sterile bowl onto the implant delivery device disposed about the at least one inclined guide portion.

Statement 91: The method according to any one of Statements 79-90, further comprising: wetting the implant delivery device by pouring a liquid wetting solution onto the implant delivery device when the implant delivery device is disposed about the loading apparatus, such that the liquid wetting solution drains into the reservoir and/or the receiving portion, the reservoir serving as a reservoir for the liquid wetting solution.

Statement 92: The method according to Statement 91, wherein the wetting of the implant delivery device is performed prior to depositing the implant onto the implant delivery device.

Statement 93: The method according to any one of Statements 79-92, wherein the implant delivery device comprises: a delivery member having an upper surface and a lower surface, the delivery member having an aperture formed therein and extending through the upper surface and the lower surface; and a shielding member coupled with the delivery member, the shielding member having an inner bore extending longitudinally between a proximal end having a proximal opening and a distal end having a distal opening, the inner bore extending a predetermined length away from the lower surface of the delivery member; wherein the proximal end of the shielding member is coupled with the delivery member and the inner bore is substantially aligned with the aperture formed in the delivery member.

Statement 94: The method according to Statement 93, wherein at least a portion of the shielding member of the implant delivery device is received in the receiving portion and at least a portion of the delivery member of the implant delivery device is disposed about the at least one inclined guide portion.

Statement 95: The method according to Statement 93 or Statement 94, further comprising: causing the implant delivery device to be placed on the loading apparatus such that at least a portion of the shielding member of the implant delivery device is received in the receiving portion and at least a portion of the delivery member of the implant delivery device is disposed about the at least one inclined guide portion.

Statement 96: The method according to Statement 94 or Statement 95, further comprising: depositing an implant onto the upper surface of the delivery member, or portion thereof, of the implant delivery device disposed about the at least one inclined guide portion such that the implant is caused to slide down the at least one inclined guide portion towards the receiving portion such that at least a portion of the leading edge of the implant is received into the proximal end of the shielding member or the inner bore of the shielding member received in the receiving portion.

What is claimed is:

1. A loading apparatus for facilitating the loading of an implant into an implant delivery device, the apparatus comprising:
    a receiving portion operable to receive at least a portion of the implant delivery device such that movement of the implant delivery device is mitigated during loading of an implant into the delivery device or onto a surface of the delivery device; and
    a pop-up portion operable to deploy from a substantially flat undeployed first configuration to an extended deployed second configuration, the extended second configuration comprising at least one inclined guide portion;
    wherein the implant delivery device is operable to deliver an implant into a surgically-created implant pocket in a subject.

2. The loading apparatus according to claim 1, wherein the receiving portion is configured to receive a distal end of the implant delivery device.

3. The loading apparatus according to claim 2, wherein the receiving portion comprises a shape that is complementary to a shape of the distal end of the implant delivery device so that the receiving portion is configured to receive the distal end of the implant delivery device.

4. The loading apparatus according to claim 3, wherein the receiving portion is operable to positionally fix or stabilize the implant delivery device during loading when the implant delivery device or a portion thereof is received in the receiving portion.

5. The loading apparatus according to claim 4, wherein the receiving portion comprises a retaining ring that is under tension such that when the implant delivery device or a portion thereof is received in the receiving portion, the tension is operable to resist movement of the implant delivery device during loading.

6. The loading apparatus according to claim 5, wherein the receiving portion comprises one or more walls, wherein the one or more walls forms a cavity or channel operable to receive the distal end of the implant delivery device, or a portion thereof, and wherein the one or more walls forms a recessed receiving portion operable to receive the distal end of the implant delivery device, or a portion thereof, therein.

7. The loading apparatus according to claim 1, wherein the pop-up portion comprises:
    a first extendable member coupled to a first elevatable member; and
    a second extendable member coupled to a second elevatable member;
    the pop-up portion operable such that when the first and second extendable members are extended, the first and second elevatable members are elevated to each form the at least one inclined guide portion and an opposing inclined guide portion, respectively, such that the at least one inclined guide portion and the opposing inclined guide portions substantially form a U-shape or a V-shape with respect to an upper surface of the tray portion.

8. The loading apparatus according to claim 7, wherein the first extendable member is coupled to a first push or pull tab and the second extendable member is coupled to a second push or pull tab, the first and second extendable members configured to extend upon application of force to a respective one of the first and second push or pull tabs; wherein the pop-up portion is operable to deploy from the substantially flat undeployed first configuration to the extended deployed second configuration upon the application of force to the first and second push or pull tabs.

9. The loading apparatus according to claim 8, wherein the pop-up portion further comprises one or more travel limiters, the one or more travel limiters coupling the first elevatable member to the second elevatable member thereby limiting travel or inclination of the first and second elevatable members during extension of the first and second extendable members.

10. The loading apparatus according to claim 7, further comprising:
    a tray portion having an upper surface, a lower surface, an outer edge extending around the upper and lower surfaces, and a wall extending around the outer edge such that the wall, together with the upper surface, forms a reservoir;
    wherein the pop-up portion is operable to be retained within the reservoir of the tray portion;
    wherein the reservoir is operable to completely contain the pop-up portion when the pop-up portion is in the substantially flat undeployed first configuration; and
    wherein the reservoir is operable to receive and retain a liquid wetting solution for wetting the delivery device.

11. The loading apparatus according to claim 10, wherein the receiving portion is a recessed receiving portion located substantially near the center of the pop-up portion;
    wherein the pop-up portion comprises an aperture substantially near the center of the pop-up portion, wherein the aperture is operable to receive the receiving portion on the tray portion; and wherein the receiving portion of the tray portion is coupled to the pop-up portion at the aperture.

12. The loading apparatus according to claim 1, wherein the pop-up portion comprises an extendable member and an elevatable member, the extendable member coupled to the elevatable member such that when the extendable member is extended the elevatable member is elevated to form the at least one inclined guide portion;
    wherein the extendable member is folded beneath the elevatable member when the pop-up portion is in the substantially flat undeployed first configuration;
    wherein the pop-up portion is operable to deploy from the substantially flat undeployed first configuration to the extended deployed second configuration, the extended deployed second configuration comprising one or more inclined surfaces in the form of the at least one inclined guide portion operable to receive at least a portion of the implant delivery device;
    wherein the at least one inclined guide portion is operable to receive the portion of the delivery device when the implant delivery device, or a portion thereof, is received in the receiving portion;
    wherein when the implant delivery device or at least a portion thereof is received in a recessed receiving portion of the receiving portion, the at least one inclined guide portion is operable to receive the implant and guide it toward the recessed receiving portion such that at least a portion of the implant is received in the implant delivery device, or a portion thereof, received in the recessed receiving portion; and wherein the recessed receiving portion is operable to receive the implant, or a portion thereof, such that the implant is oriented properly in the implant delivery device.

13. A system for facilitating the loading of an implant into an implant delivery device, the system comprising: a loading apparatus comprising: a receiving portion operable to receive at least a portion of the implant delivery device such that movement of the implant delivery device is mitigated during loading of an implant into the implant delivery device or onto a surface of the implant delivery device; and a pop-up portion operable to deploy from a substantially flat undeployed first configuration to an extended deployed second configuration, the extended deployed second configuration comprising at least one inclined guide portion; and the implant delivery device is operable to deliver the implant into a surgically-created implant pocket in a subject.

14. The system according to claim 13, wherein the pop-up portion comprises:
 a first extendable member coupled to a first elevatable member; and
 a second extendable member coupled to a second elevatable member;
 the pop-up portion operable such that when the first and second extendable members are extended, the first and second elevatable members are elevated to each form the at least one inclined guide portion and an opposing inclined guide portion, respectively, such that the at least one inclined guide portion and the opposing inclined guide portion substantially form a U-shape or a V-shape with respect to an upper surface of the tray portion.

15. The system according to claim 14, further comprising an implant; wherein the at least one inclined guide portion is configured to receive the implant and provide for translation of the implant down the at least one inclined guide portion towards the receiving portion such that at least a portion of the implant is received into the portion of the implant delivery device received in the receiving portion.

16. A method of loading an implant into an implant delivery device, the method comprising:
 providing a loading apparatus having a receiving portion operable to receive at least a portion of the implant delivery device, the loading apparatus having at least one inclined guide portion;
 providing the implant delivery device having a proximal end operable for receiving the implant during loading and a distal end operable to be contacted with an incision in a subject during delivery of the implant into an implant pocket in the subject, wherein at least a portion of the proximal end of the implant delivery device is disposed about the at least one inclined guide portion and at least a portion of the distal end of the implant delivery device is received in the receiving portion;
 depositing the implant onto the proximal end, or portion thereof, of the implant delivery device disposed about the at least one inclined guide portion such that the implant is caused to translate down the at least one inclined guide portion towards the receiving portion such that at least a portion of a leading edge of the implant is received into the distal end of the implant delivery device received in the receiving portion.

17. The method according to claim 16, wherein the loading apparatus further comprises:
 a pop-up portion operable to deploy from a substantially flat undeployed first configuration to an extended deployed second configuration, the extended deployed second configuration comprising the at least one inclined guide portion; and
 the method further comprises:
  causing the pop-up portion to deploy from the substantially flat undeployed first configuration to the extended deployed second configuration having the at least one inclined guide portion.

18. The method according to claim 17, wherein causing the pop-up portion to deploy comprises the application of force to one or more push or pull tabs coupled with the pop-up portion.

19. The method according to claim 17, further comprising:
 causing the pop-up portion to deploy from the substantially flat undeployed first configuration to the extended deployed second configuration having the plurality of inclined guide portions, the plurality of inclined guide portions arranged in opposition to substantially form a U-shape or a V-shape configured to receive at least the portion of the proximal end of the implant delivery device; and causing the implant delivery device to be placed on the loading apparatus such that at least the portion of the distal end of the implant delivery device is received in the receiving portion and at least the portion of the proximal end of the implant delivery device is disposed about the at least one inclined guide portion.

* * * * *